(12) United States Patent
Huang et al.

(10) Patent No.: US 11,987,556 B2
(45) Date of Patent: May 21, 2024

(54) DUAL-FUNCTIONAL COMPOUNDS AND METHODS OF USE

(71) Applicant: BIOFRONT THERAPEUTICS (BEIJING) CO., LTD., Beijing (CN)

(72) Inventors: Zheng Huang, Beijing (CN); Tianwei Ma, Beijing (CN)

(73) Assignee: BIOFRONT THERAPEUTICS (BEIJING) CO., LTD., Beijing (CN)

( * ) Notice: Subject to any disclaimer, the term of this patent is extended or adjusted under 35 U.S.C. 154(b) by 0 days.

(21) Appl. No.: 18/161,843

(22) Filed: Jan. 30, 2023

(65) Prior Publication Data

US 2023/0174482 A1 Jun. 8, 2023

Related U.S. Application Data

(63) Continuation of application No. PCT/CN2021/109492, filed on Jul. 30, 2021.

(60) Provisional application No. 63/058,512, filed on Jul. 30, 2020.

(51) Int. Cl.
| | |
|---|---|
| C07D 209/38 | (2006.01) |
| A61P 11/00 | (2006.01) |
| C07D 497/04 | (2006.01) |

(52) U.S. Cl.
CPC ............ *C07D 209/38* (2013.01); *A61P 11/00* (2018.01); *C07D 497/04* (2013.01)

(58) Field of Classification Search
None
See application file for complete search history.

(56) References Cited

U.S. PATENT DOCUMENTS

| | | | |
|---|---|---|---|
| 5,958,926 A | 9/1999 | Garvey et al. | |
| 6,020,358 A * | 2/2000 | Muller | A61P 29/00 514/416 |
| 6,133,272 A | 10/2000 | Garvey et al. | |
| 6,331,543 B1 | 12/2001 | Garvey et al. | |
| 6,472,425 B1 | 10/2002 | Garvey et al. | |
| 7,345,037 B2 | 3/2008 | Garvey et al. | |
| 10,344,002 B2 | 7/2019 | Zemel et al. | |
| 2008/0009498 A1 | 1/2008 | Garvey et al. | |
| 2009/0215838 A1 | 8/2009 | Garvey et al. | |
| 2018/0312513 A1 | 11/2018 | Naef et al. | |
| 2021/0322413 A1 | 10/2021 | Almirante et al. | |

FOREIGN PATENT DOCUMENTS

| | | |
|---|---|---|
| CN | 113767104 A | 12/2021 |
| WO | 9819672 A1 | 5/1998 |
| WO | 2012083153 A1 | 6/2012 |
| WO | 2014204825 A1 | 12/2014 |
| WO | 2020185674 A1 | 9/2020 |

OTHER PUBLICATIONS

The Extended European Search Report in European Application No. 21851360.4 dated Oct. 12, 2023, 8 pages.
International Search Report in PCT/CN2021/109492 dated Oct. 26, 2021, 7 pages.
Written Opinion in PCT/CN2021/109492 dated Oct. 26, 2021, 7 pages.
International Search Report in PCT/CN2022/074797 dated Apr. 28, 2022, 8 pages.
Written Opinion in PCT/CN2022/074797 dated Apr. 28, 2022, 8 pages.
Haroldo A. Flores Toque et al., Synthesis and Pharmacological Evaluations of Sildenafil Analogues for Treatment of Erectile Dysfunction, J. Med. Chem., 51(9): 2807-2815, 2008.

\* cited by examiner

*Primary Examiner* — Samantha L Shterengarts
(74) *Attorney, Agent, or Firm* — METIS IP LLC

(57) ABSTRACT

The present disclosure provides a compound configured to release nitric oxide (NO) and inhibit the activity of a phosphodiesterase (PDE) when administered to a subject. The compound may include $L_1$ and $L_2$. $L_1$ may include a functional group that is part or all of a NO releasing agent. $L_2$ may include a functional group that is part or all of a PDE inhibitor. The compound may further include a bond or a biradical that connects $L_1$ and $L_2$. The present disclosure further provides a method of treating or preventing a disease using the compound or a composition including the compound.

17 Claims, 14 Drawing Sheets

Cilomilast

Apremilast

Cilostazol

Pentoxifyline

Roflumilast

Dipyridamole

DUAL-FUNCTIONAL COMPOUNDS AND METHODS OF USE

CROSS-REFERENCE TO RELATED APPLICATIONS

This application is a continuation of International Application No. PCT/CN2021/109492, filed on Jul. 30, 2021, which claims priority to U.S. Provisional Application No. 63/058,512, filed on Jul. 30, 2020, the entire contents of each of which are hereby incorporated by reference.

TECHNICAL FIELD

The present disclosure generally relates to dual-functional compounds and methods of use, and in particular, to compounds capable of releasing nitric oxide (NO) and inhibiting activity of a phosphodiesterase (PDE) and methods of treating diseases or disorders using the compounds.

BACKGROUND

Acute lung injury (ALI) and Acute respiratory distress syndromes (ARDS) are clinically important diseases due to their high morbidity and mortality. ARDS is a common cause of respiratory failure characterized by rapidly progressive pulmonary edema, reduced lung compliance and hypoxemia. ARDS is often caused by infection, insult or trauma, including viral and bacterial pneumonia, neurogenic edema, viral or bacterial sepsis (e.g., with sources from the peritoneum, urinary tract, or soft tissue), pancreatitis, graft dysfunction after transplantation, etc. Moreover, ARDS is one of the major causes of death from the recurring severe viral infections such as severe influenzas, the severe acute respiratory syndrome coronavirus 1 (SARS-CoV-1), Middle East Respiratory Syndrome (MERS), and SARS-CoV-2. Patients suffering from severe coronavirus disease 2019 (COVID-19) have a high mortality, especially among the elder persons who also suffer from microvascular disorders including those with diabetes, chronic kidney disease, heart disease, and/or other disorders. The efficacy of existing therapies for the treatment or prevention of ARDS are limited. Thus, it is desirable to develop more effective therapeutic compositions and methods for treating ARDS.

SUMMARY

According to an aspect of the present disclosure, a compound represented by formula (I): $L_1$-X-$L_2$ (I) is provided. The compound may be configured to release nitric oxide (NO) and inhibit activity of a phosphodiesterase (PDE) when administered to a subject. $L_1$ may include a functional group that is part or all of a NO releasing agent. $L_2$ may include a functional group that is part or all of a PDE inhibitor. —X— may be a covalent bond, a non-covalent bond or a biradical that connects $L_1$ and $L_2$.

In some embodiments, $L_2$ may be derived from apremilast.

In some embodiments, $L_2$ may be

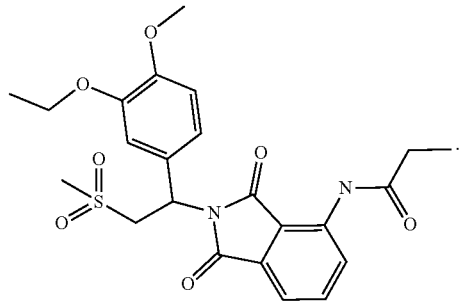 [SMILES: CCOc1cc(C(CS(C)(=O)=O)N2C(=O)c3cccc(NC(=O)CC)c3C2=O)ccc1OC]

In some embodiments, $L_1$ may be —C(CH$_3$)$_2$—CH$_2$—ONO$_2$.

In some embodiments, $L_1$ may be —C(CH$_3$)—(CH$_2$—ONO$_2$)$_2$.

According to another aspect of the present disclosure, a compound represented by formula (II) is provided. —X— may be a covalent bond, a non-covalent bond, or a biradical. $L_1$ may include a functional group that is part or all of a nitric oxide (NO) releasing agent.

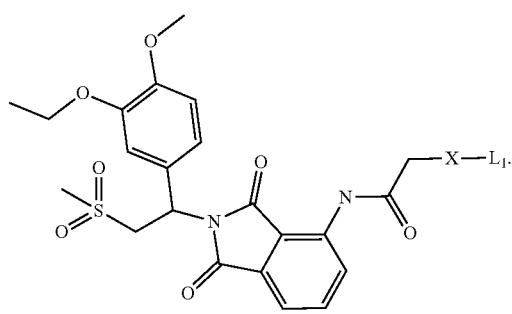

(II)

In some embodiments, X may include O, C, N, S, or P.

In some embodiments, X may include 0-10 atoms.

In some embodiments, —X— may include an ester bond, an amide bond, a sulfonamide bond, a sulfate bond, a phosphoramide bond, a phosphate bond, ketonic bond, or an arylene group.

In some embodiments, $L_1$ may include one or more —ONO$_2$ groups.

In some embodiments, $L_1$ may be —C(CH$_3$)$_2$—CH$_2$—ONO$_2$.

In some embodiments, the compound may be

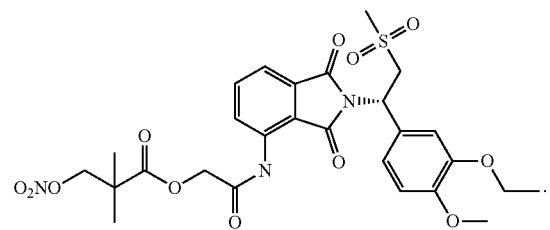

In some embodiments, the compound may be

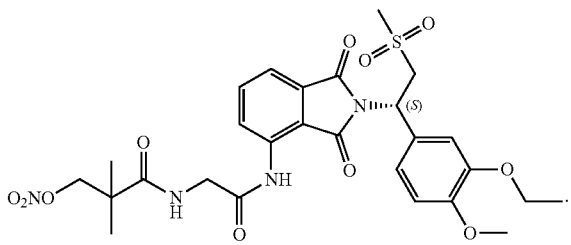

In some embodiments, $L_1$ may be —C(CH$_3$)—(CH$_2$—ONO$_2$)$_2$.

In some embodiments, the compound may be

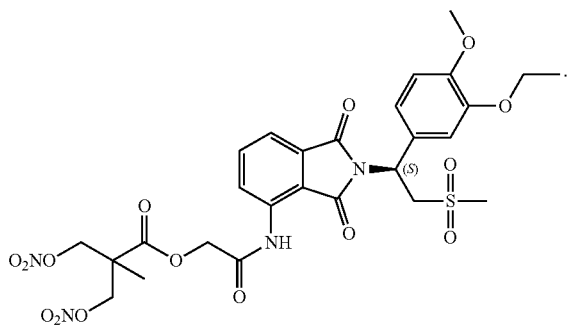

In some embodiments, the compound may be

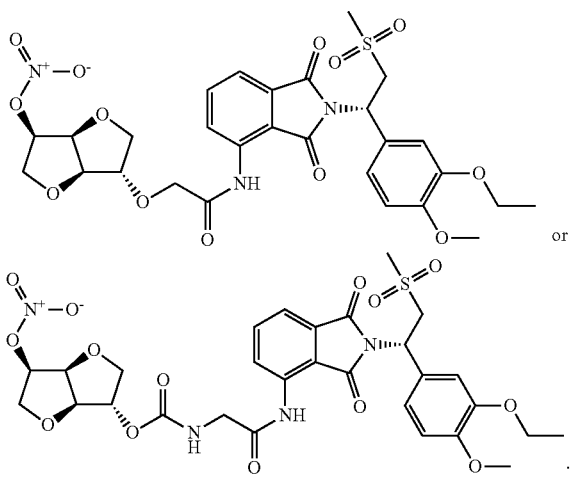

In some embodiments, the NO releasing agent may be nitroglycerin (GTN), isosorbide dinitrate (ISDN), or pentaerythritol tetranitrate (PETN).

In some embodiments, the compound may be configured to release NO and inhibit activity of a phosphodiesterase (PDE) when administered to a subject.

In some embodiments, the PDE may include PDE4.

According to another aspect of the present disclosure, a composition comprising the compound of any one described above and a pharmaceutically acceptable carrier is provided.

In some embodiments, the composition may be formulated as a tablet, a capsule, granules, powder, micelles, liquid, suspension, cream, foam, gels, lotion, pastes, or ointment.

In some embodiments, the composition may be administered to a subject through at least one of an oral administration, an injection administration, or a topical administration.

According to a further aspect of the present disclosure, a use of the compound of any one described above for treating or preventing a phosphodiesterase (PDE)-related disease in a subject.

According to a further aspect of the present disclosure, a use of the compound of any one described above for treating or preventing cancer in a subject.

According to a further aspect of the present disclosure, a use of the compound of any one described above for treating or preventing acute lung injury (ALI) or acute respiratory distress syndrome (ARDS).

In some embodiments, the compound may release NO and inhibit activity of phosphodiesterase (PDE) in local tissues after the compound is administered to the subject.

In some embodiments, the compound is further configured to use a tunable nitric oxide releasing property to modulate the delivery of PDE4 inhibitor into the vasculature or near vasculature space.

According to yet another aspect of the present disclosure, a method of treating or preventing acute lung injury (ALI) or acute respiratory distress syndrome (ARDS) in a subject is provided. The method may include administering to the subject a pharmaceutically effective amount of the compound of any one described above.

According to yet another aspect of the present disclosure, a method of treating or preventing a phosphodiesterase (PDE)-related disease in a subject. The method may include administering to the subject a pharmaceutically effective amount of the compounds of any one described above.

According to yet another aspect of the present disclosure, a method of treating or preventing a phosphodiesterase-4 (PDE4)-related disease in a subject. The method may include administering to the subject a pharmaceutically effective amount of the compound of any one described above.

In some embodiments, administering to the subject the pharmaceutically effective amount of the compound may include orally administering the compound to the subject at 0.01-50 mg/kg.

In some embodiments, administering to the subject the pharmaceutically effective amount of the compound may include orally administering the compound to the subject at 1-50 mg/kg.

In some embodiments, administering to the subject the pharmaceutically effective amount of the compound may include orally administering the compound to the subject at 5-50 mg/kg.

In some embodiments, the compound may exhibit a half maximal inhibitory concentration (IC50) of less than 720 nM for inhibiting PDE4A.

In some embodiments, the compound may exhibit a half maximal inhibitory concentration (IC50) of less than 200 nM for inhibiting PDE4A.

In some embodiments, the compound may exhibit a half maximal inhibitory concentration (IC50) of less than 2.3 μM for inhibiting PDE4C.

In some embodiments, the compound may exhibit a half maximal inhibitory concentration (IC50) of less than 0.7 μM for inhibiting PDE4C.

In some embodiments, after the compound is administered to the subject, a level of plasma nitrate in the subject may be increased.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. It should be noted that the drawings are not to scale. These embodiments are non-limiting exemplary embodiments, in which like reference numerals represent similar structures throughout the several views of the drawings, and wherein.

DETAILED DESCRIPTION

Figure 1A:
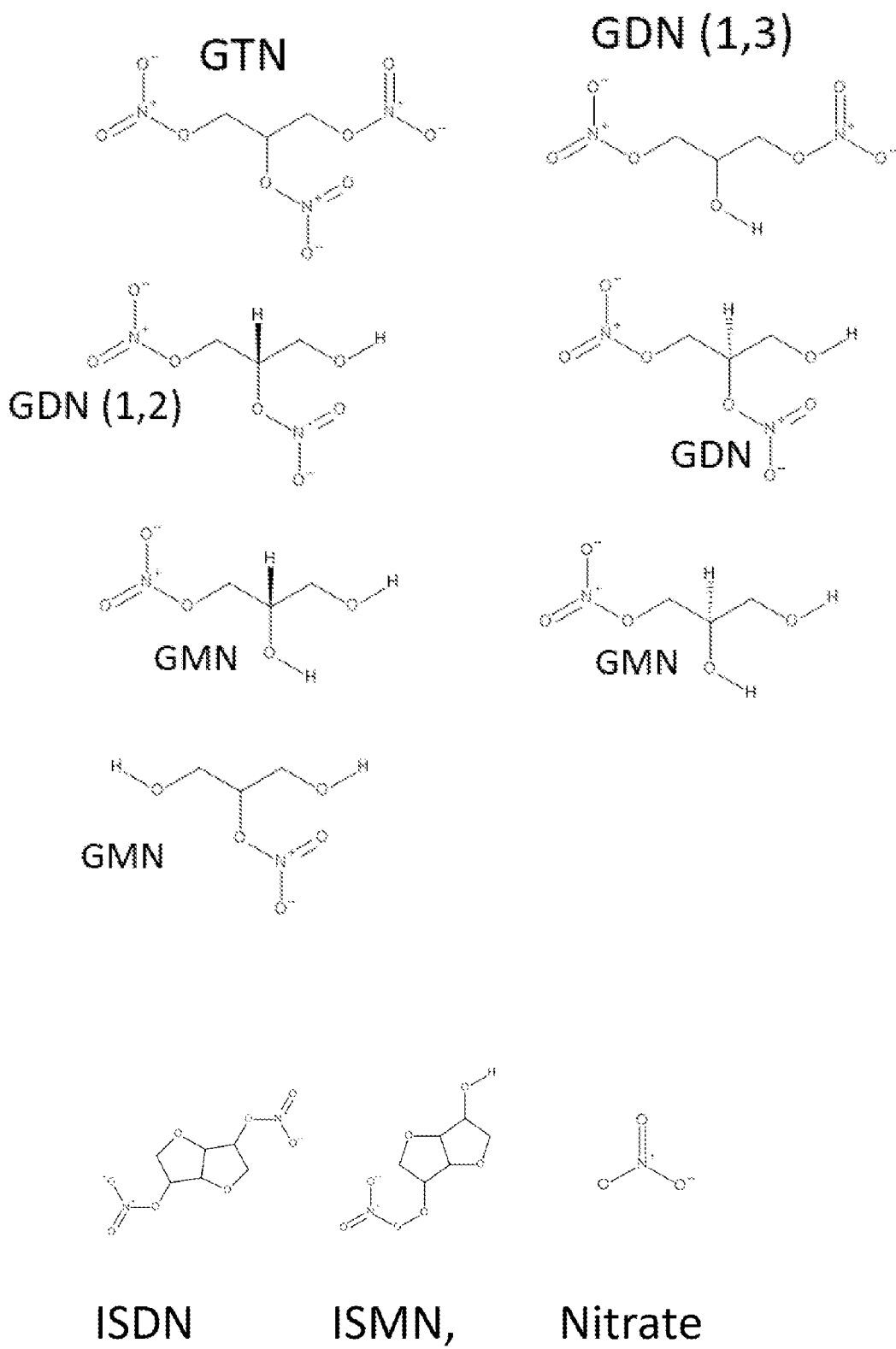
FIGS. 1A-1B are diagrams illustrating structural formulas of exemplary organic nitrates that can release NO according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. It is understood that the drawings are not to scale.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

According to an aspect of the present disclosure, one or more compounds are provided. A representative compound may be configured to release nitric oxide (NO) and inhibit the activity of a phosphodiesterase (PDE) when administered to a subject. In some embodiments, the subject is a human. In some embodiments, the subject is a non-human animal. In some embodiments, the subject is male. In some embodiments, the subject is female. In some embodiments, the subject is suffering from a disease or pathological condition.

In some embodiments, the compound may be represented by formula (I):

$$L_1\text{-}X\text{-}L_2 \qquad (1)$$

where $L_1$ may include a functional group that is part or all of a NO releasing agent; $L_2$ may include a functional group that is part or all of a PDE inhibitor; and —X— may be a bond or a biradical that connects $L_1$ and $L_2$. As discussed here, the "NO releasing agent" refers to an agent that is capable of releasing NO in a controlled or uncontrolled manner; the "PDE inhibitor" refers to a molecular or agent that is capable of inhibiting PDE activities. $L_1$ may enable the compound to release NO via bioactivation. $L_2$ may enable the compound to inhibit the activity of PDE. In some embodiments, $L_1$ and $L_2$ may be connected via —X—. For example, —X— may be a covalent bond or a non-covalent bond. The non-covalent bond may include an ionic bond, a metallic bond, a hydrogen bond, a hydrophobic interaction, or the like, or any combination thereof. As another example, —X— may be a biradical that connects $L_1$ with $L_2$. The biradical may be a branched or unbranched, saturated or unsaturated, substituted or unsubstituted hydrocarbon group (such as a $C_{1-50}$ chain). In some embodiments, if the hydrocarbon group is substituted, the hydrocarbon group may be substituted by one or more heteroatoms, such as N, P, S, O, or the like, or any combination thereof. For example, the substituted hydrocarbon group may be substituted by a heterochain group (e.g., —$NH_3$, —COOH or —OH) or a heterocyclic group (e.g., a phenolic group, an anilino group). In some embodiments, —X— may be an aromatic moiety, a fused aromatic moiety, sugar, oligo-saccharide, ethylene glycol, polyethylene glycol, peptide bond, or the like.

Nitric oxide (NO) is one of the main endogenous regulators of blood flow and hemodynamics. For instance, NO may facilitate vasodilation, improve capillary blood flow and oxygen supply in a hypoxic state. NO may also protect vasculature damage and help repair vessel injury. NO also inhibit virus or bacteria infection. However, the half-life of NO in the body is short (only a few milliseconds), which greatly limits the use of exogenous NO to treat virus or bacteria infection, to repair vasculature injury related diseases. In addition, inhaled NO has limited efficacy for ARDS from its poor tissue penetration. High dose of inhaled NO reacts with reactive oxygen species (ROS) and forms toxic reactive nitrogen species (RNS) metabolites, leading to vasculature injury and excessive inflammation.

Since $L_1$ includes a functional group that is part or all of the NO releasing agent, the exemplary compound disclosed in this invention may continuously release NO in local tissues through bioactivation (or metabolic activation). For example, the compounds may release NO due to the reductant effect of one or more reductases, such as dehydrogenase(s), glutathione S-transferases (GSTs), P450s.

Figure 1B:
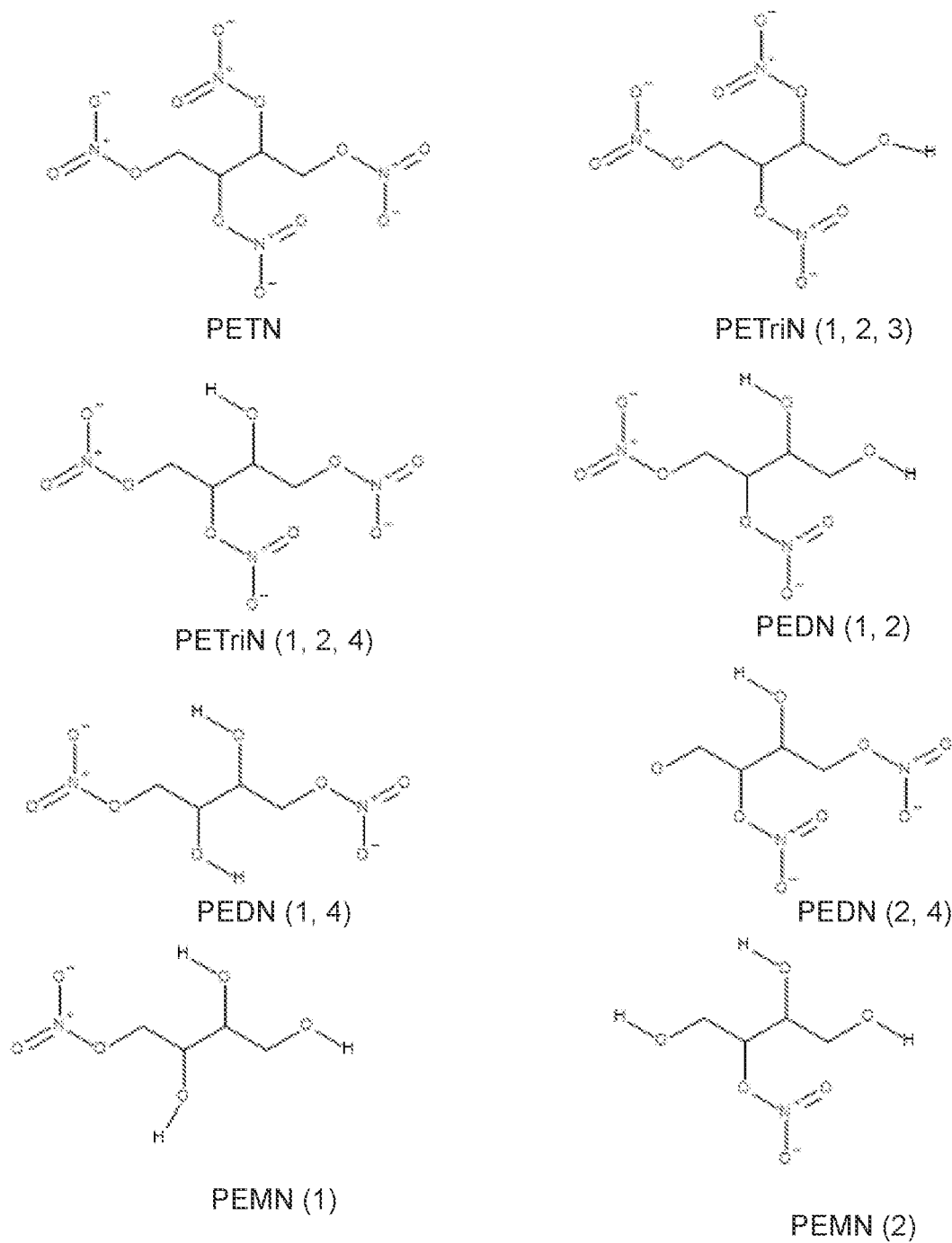

In some embodiments, the NO releasing agent may be an organic nitrate ester. Organic nitrate is a prodrug of NO. The compound including $L_1$ (which includes the functional group that is part of or all of the organic nitrate) may release NO continuously—via bioactivation, and the released NO can penetrate into nearby tissues. The organic nitrate refers to nitric acid esters of alcohol groups. Commonly used organic nitrates include glyceryl trinitrate (GTN), glyceryl dinitrate (GDN), glyceryl mononitrate (GMN), pentaerythritol tetranitrate (PETN), pentaerythritol trinitrate (PETriN), pentaerythritol dinitrate (PEDN), pentaerythritol mononitrate (PEMN), isosorbide dinitrate (ISDN), isosorbide mononitrate (ISMN), Nicorandil, propatylnitrate, Sinitrodil, tenitramine, trolnitrate, etc. FIGS. 1A-1B are diagrams illustrating structural formulas of exemplary organic nitrates that can release NO according to some embodiments of the present disclosure. For instance, GDN may include structural isomers such as GDN (1, 3), GDN (1, 2), and stereoisomers as shown in FIG. 1A. GMN may also include some stereoisomers. As another example, PETriN, PEDN, and PEMN may include structural isomers, respectively, as shown in FIG. 1B. $L_1$ may also include a functional group that is part or all of the structural isomers or stereoisomers of the organic nitrate.

Figure 1C:
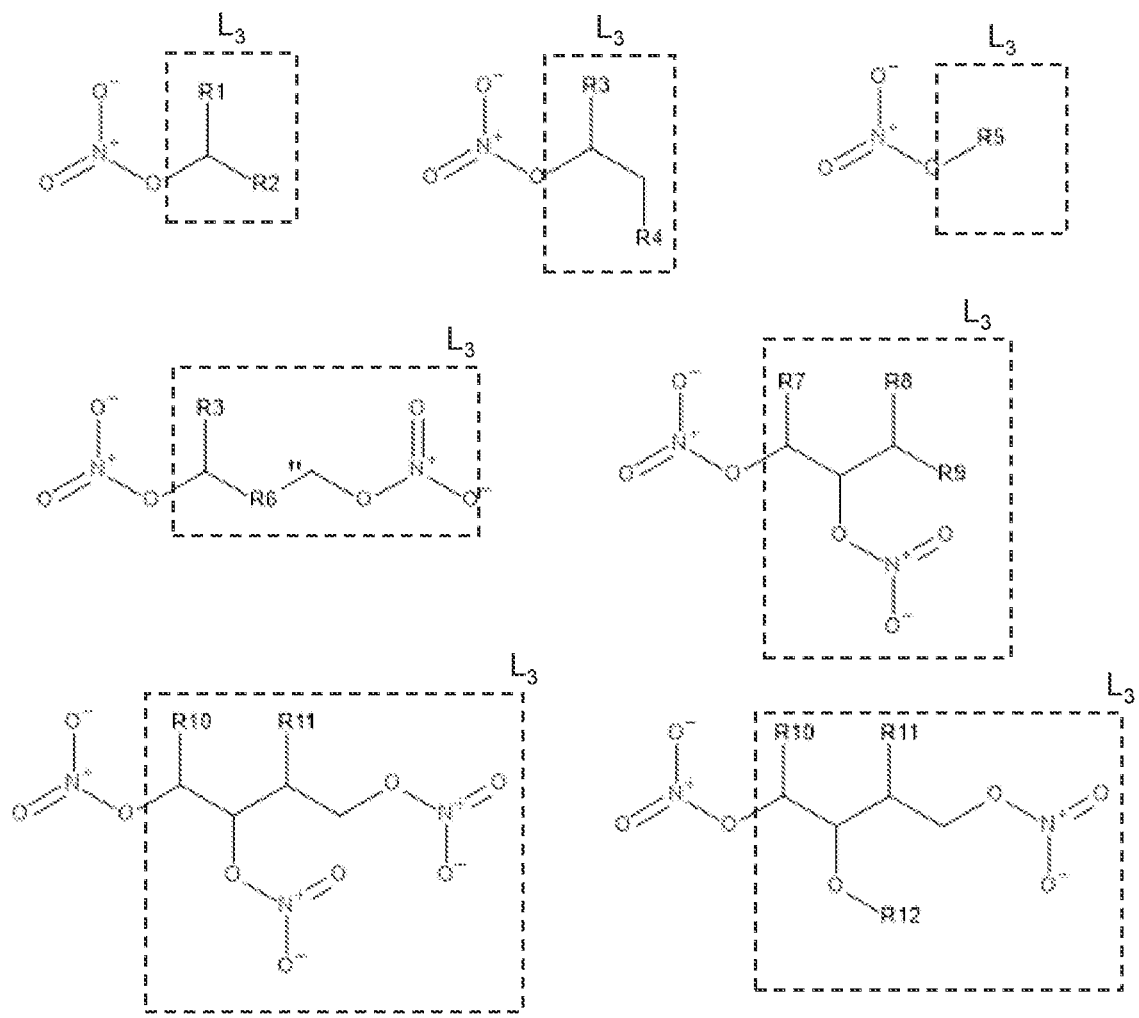
FIG. 1C is a diagram illustrating exemplary structural formulas of $L_1$ including a functional group that is part or all of an organic nitrate according to some embodiments of the present disclosure.

In some embodiments, $L_1$ may be presented by a general formula $L_3$-$ONO_2$. $L_3$ may be, for example, an aryl, a benzyl, or a primary, a secondary, or a tertiary alkyl group. $L_3$ may be unsubstituted or substituted by one or more heteroatoms. As yet another example, $L_3$ may be saturated or unsaturated. When $L_3$ is unsaturated, $L_3$ may include one or more double bonds and/or one or more triple bonds. Merely by way of example, $L_3$ may be a $C_{1-99}$ carbon chain that is unsubstituted or substituted by one or more heteroatoms, such as N, P, S, O, etc. For instance, if $L_3$ is substituted, $L_3$ may be substituted by a heterochain group (e.g., —$NH_3$, —COOH or —OH) or a heterocyclic group (e.g., a phenolic group, an anilino group). As yet another example, $L_3$ may be branched or unbranched. In some embodiments, $L_3$ may include one or more —$ONO_2$ groups. FIG. 1C is a diagram illustrating exemplary structural formulas of $L_1$ including a functional group that is part or all of an organic nitrate according to some embodiments of the present disclosure. As shown in FIG. 1B, $R_1$-$R_{12}$ may respectively be a branched or unbranched, saturated or unsaturated, substituted or unsubstituted hydrocarbon group.

Figure 1D:
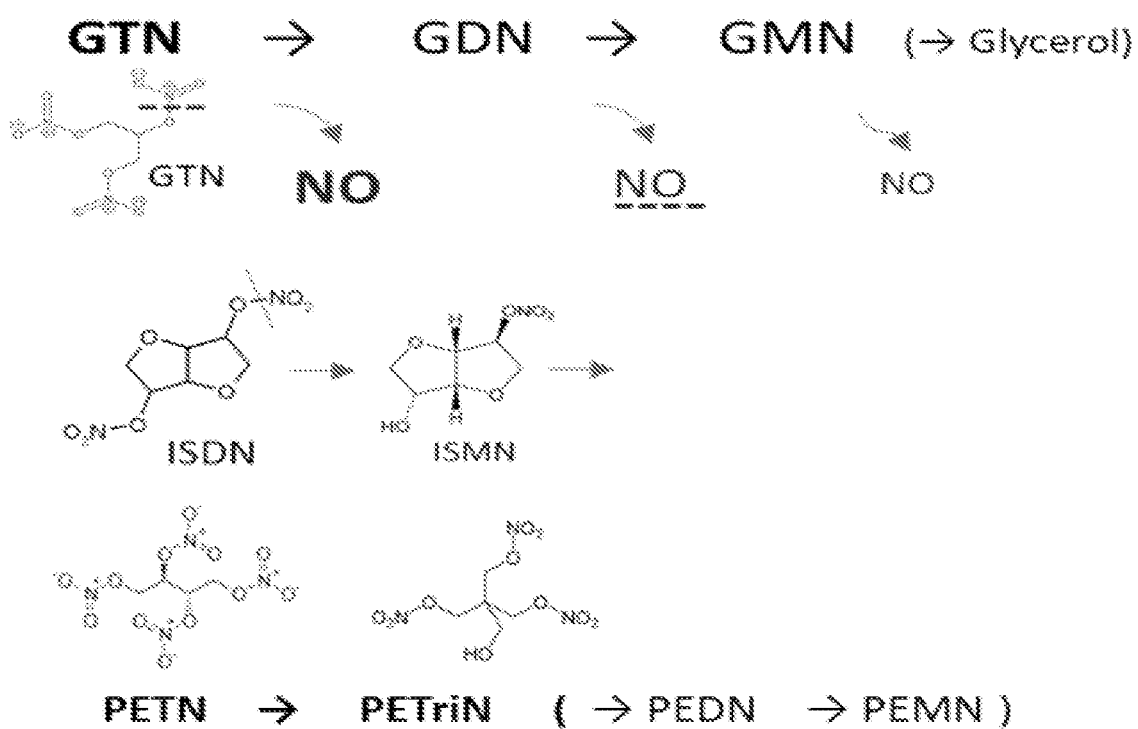
FIG. 1D is a diagram illustrating the releasing of NO by exemplary NO releasing agents according to some embodiments of the present disclosure.

FIG. 1D is a diagram illustrating the releasing of NO by exemplary NO releasing agents according to some embodiments of the present disclosure. A NO releasing molecule may be able to release one or more NO molecules through bioactivation (e.g., by a reductase) in the cell or the tissue. As shown in FIG. 1D, a GTN molecule may release a NO molecule and be transformed into a GDN molecule. A GDN molecule may release a NO molecule and be transformed into a GMN molecule. Similarly, an ISDN molecule may release a NO molecule and be transformed into an ISMN molecule. A PETN molecule may gradually release 4 NO molecules and be transformed to PETriN, PEDN, and PEMN, as shown in FIG. 1D. In some embodiments, $L_1$ may include multiple functional groups related to the releasing of NO. The compounds may continuously release NO in local tissue. For example, $L_1$ may include 1 nitrate ester group, 2 nitrate ester group, 3 nitrate ester groups, or 4 nitrate ester groups. As another example, $L_1$ may include 5 nitrate ester groups. As yet another example, $L_1$ may include an inorganic nitrate. For example, the inorganic nitrate may include a nitrate salt, such as potassium nitrate, sodium nitrate, etc. $L_1$ may be a nitrite or a nitrite salt.

The 3',5'-cyclic nucleotide phosphodiesterases (PDE) degrade the second messengers cyclic adenosine monophosphate (cAMP) and cyclic guanosine monophosphate (cGMP). The PDEs contain 11 gene families (PDE1, PDE2, PDE3, PDE4, PDE5, PDE6, PDE7, PDE8, PDE9, PDE10, and PDE11). Each member of the PDE enzyme family has its own substrate preference for cAMP and/or cGMP, tissue distribution, and is regulated by specific cofactors and activators. PDE1, PDE2, PDE3, PDE10 and PDE11 degrade both cAMP and cGMP. PDE4, PDE7, and PDE8 selectively degrade cAMP. PDE5, PDE6 and PDE9 selectively degrade cGMP.

In some embodiments, $L_2$ may include a functional group that is part or all of a PDE inhibitor that inhibits the activity of PDE. As used herein, the term "activity" of an enzyme refers to the functional capability (e.g. catalyzation) of any molecules (e.g. enzymes) in a region (e.g., cellular region) or tissue. The activity may be affected by a change in the expression level of the molecule, or by a change of the functional level of per unit the molecule, or both. For example, the activity of PDE may be inhibited by decreasing the expression of PDE and/or impeding the functions of PDE.

In some embodiments, the PDE inhibitor may be a selective inhibitor that inhibits a particular member of the PDE family. In some embodiments, the PDE inhibitor may inhibit multiple members of the PDE family.

In some embodiments, the PDE may be PDE4 and the PDE inhibitor may be a PDE4 inhibitor. In some embodiments, the PDE4 inhibitor is a specific inhibitor that has a specificity that is higher than a predetermined threshold.

In some embodiments, the PDE may be PDE3 and the PDE inhibitor may be a PDE3 inhibitor. In some embodiments, the PDE may be PDE5 and the PDE inhibitor may be a PDE5 inhibitor.

In some embodiments, the PDE inhibitor may be a PDE1 inhibitor, a PDE2 inhibitor, a PDE4 inhibitor, a PDE5 inhibitor, a PDE6 inhibitor, a PDE7 inhibitor, a PDE8 inhibitor, a PDE9 inhibitor, a PDE10 inhibitor, a PDE11 inhibitor, or the like, or any combination thereof.

In some embodiments, the PDE inhibitor may be a dual PDE3/PDE4 inhibitor. In some embodiments, the PDE inhibitor may be a dual PDE4/PDE5 inhibitor. In some embodiments, the PDE inhibitor may be a dual PDE4/PDE7 inhibitor. In some embodiments, the PDE inhibitor may be a dual PDE4/PDE8 inhibitor. In some embodiments, the PDE inhibitor may be a dual PDE4/9 inhibitor. In some embodiments, the PDE inhibitor may be a dual PDE4/PDE10 inhibitor. In some embodiments, the PDE inhibitor may be a dual PDE4/PDE11 inhibitor. In some embodiments, the PDE inhibitor may be a dual PDE 4/PDE 1 inhibitor. In some embodiments, the PDE inhibitor may be a dual PDE 4/PDE 2 inhibitor.

PDE4 is one of the main cAMP degrading enzymes of alveolar endothelial and epithelial cells, vascular smooth muscle cells, macrophages, lymphocytes, neutrophils, eosinophils, etc. PDE4 inhibitors prolong cAMP-mediated signaling, reduce the release of multiple inflammatory mediators, proinflammatory cytokines, and the infiltration of inflammatory cells into alveoli, stimulate the secretion of epithelial mucus, and promote the removal of microorganisms and cell debris. PDE4 inhibitors are effective in ARDS models and are used in the treatment of chronic obstructive pulmonary disease (COPD), psoriasis, and eczema. For instance, PDE4 inhibitors may include Roflumilast, Apremilast, Crisaborole, Cilomilast, CDP-840, MK0359, MK0873, MK0952, Ibudilast, CHF6001, Ronomilast, Oglemilast, Tetomilast, GSK256066, YM976, GS-5759, GPD-1116, MEM1414, RPL554, ASP3258, E6005, GW842470X, OPA-15406, Leo-29102, HFP034, CBS3596, Revamilast (GRC4039), NCS613, FCPP03, BAY 19-8004, CI-1004, L-791,943, L-826,141, T-2585, YM 976, Rolipram, HT-0712, ABI-4, FCPRO3, E6005 (RVT-501), GW842470X, OPA-15406, DRMO2, HFPO34, or the like, or any combination thereof.

In some embodiments, the PDE4 inhibitor may be able to inhibit the potency of at least one of PDE4A, PDE4B, PDE4C, or PDE4D. PDE5 inhibitors can block the degradative action of PDE5 on cyclic GMP in, e.g., the smooth muscle cells lining the blood vessels supplying various tissues. PDE5 inhibitors may be used as a vasodilator to improve hemodynamic regulation to treat vasoconstrictive human and animal disorders. PDE5 inhibitors such as sildenafil (Viagra), tadalafil (Cialis), avanafil (Stendra), and vardenafil (Levitra) are clinically indicated for the treatment of erectile dysfunction. Sildenafil and Tadalafil are also indicated for the treatment of some subtypes of pulmonary hypertension, while tadalafil is also licensed for the treatment of benign prostatic hyperplasia. Other exemplary PDE5 inhibitors may include mirodenafil, udenafil, lodenafil, Zaprinast, icariin, etc.

PDE3 inhibitors may be used for treating cardiac diseases and peripheral artery diseases. PDE3 inhibitors may include, for example, milrinone and cilostazol, amrinone, and enoximone. Other PDE inhibitors, including PDE7 inhibitors, may be used for treating inflammatory disorders or used as neuroprotective agents.

Figure 2:
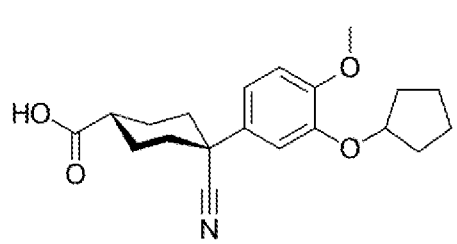
FIG. 2 is a diagram illustrating the structural formulas of the exemplary PDE4 inhibitors and PDE3 inhibitors according to some embodiments of the present disclosure.
Figure 2:
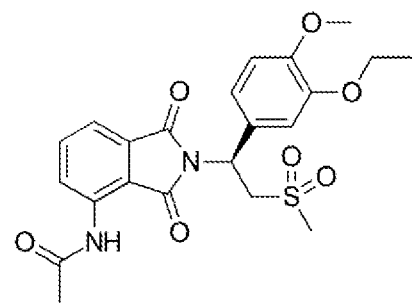
Figure 2:
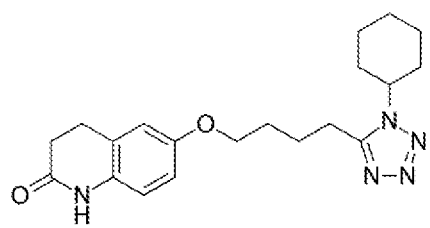
Figure 2:
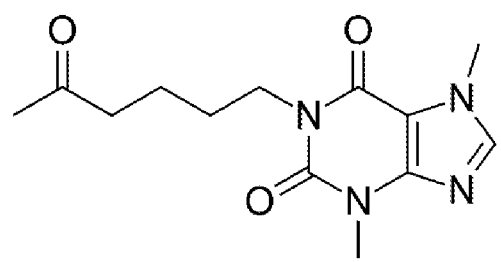
Figure 2:
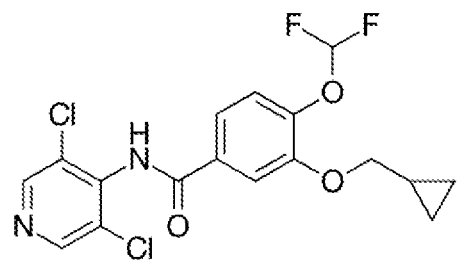
Figure 2:
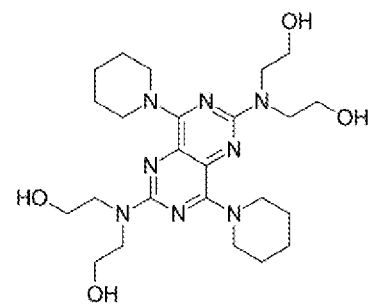

FIG. 2 is a diagram illustrating structural formulas of exemplary PDE4 inhibitors and PDE3 inhibitors according to some embodiments of the present disclosure. Included in FIG. 2 are roflumilast, which can be used to treat severe COPD, apremilast, which can be used to treat psoriatic arthritis (PsA), cilomilast, which can be used to treat respiratory disorders such as asthma and COPD, pentoxifylline, which can be used to improve blood circulation, and cilostazol, which can be used to treat peripheral vascular disease.

In some embodiments, —X— may be a bond or a diradical for connecting $L_1$ and $L_2$, and the compound may be produced based on chemical reactions involving the NO releasing—moiety and the PDE inhibiting moiety. For example, the compound may be produced based on an addition reaction, an elimination reaction, a substitution reaction, a pericyclic reaction, a rearrangement reaction, a photochemical reaction, a redox reaction, or the like, or any combination thereof.

In some embodiments, the compound may be produced using a core scaffold. In some embodiments, the core scaffold does not include $L_1$ or $L_2$. The compound may be produced by grafting $L_1$ and $L_2$ onto the core scaffold. For instance, the core scaffold may be a branched or unbranched, saturated or unsaturated, substituted or unsubstituted compound. In some embodiments, the core scaffold may include $L_1$ or $L_2$. For example, the PDE4 inhibitor including $L_2$ may be used as the core scaffold. $L_1$ may be grafted onto the PDE4 inhibitor to produce the compound. Similarly, the NO releasing compound including $L_1$ may be used as the core scaffold. $L_2$ may be grafted onto the NO releasing compound to produce the compound.

In some embodiments, $L_2$ may be derived from apremilast. In some embodiments, $L_2$ is

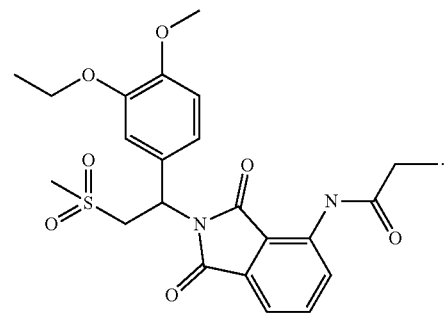 [SMILES: CCOc1cc(C(CS(C)(=O)=O)N2C(=O)c3cccc(NC(=O)CC)c3C2=O)ccc1OC]

In some embodiments, the compound may be represented by formula (II):

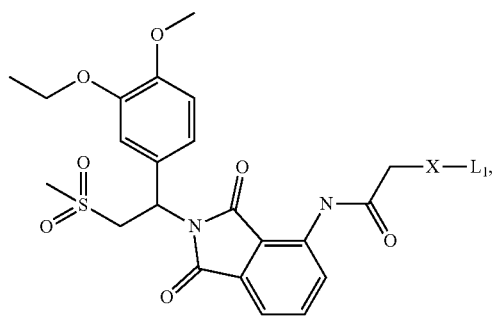

where —X— is a covalent bond, a non-covalent bond or a biradical; and $L_1$ includes a functional group that is part or all of a NO releasing agent. More description of the NO releasing agent may be found in the above description.

In some embodiments, the NO releasing agent is nitroglycerin (GTN), isosorbide dinitrate (ISDN), or pentaerythritol tetranitrate (PETN).

In some embodiments, $L_1$ may include one or more —$ONO_2$ groups. For example, $L_1$ may include one, two, or three —$ONO_2$ groups. In some embodiments, $L_1$ may be —$C(CH_3)_2$—$CH_2$—$ONO_2$, —$C(CH_3)$—$(CH_2$—$ONO_2)_2$, or the like.

In some embodiments, X may include O, C, N, S, or P. In some embodiments, X includes 0-10 atoms. In some embodiments, —X— may include an ester bond, an amide bond, a sulfonamide bond, a sulfate bond, a phosphoramide bond, a phosphate bond, ketonic bond, or an arylene group.

In some embodiments, the compound may be (S)-2-((2-(1-(3-ethoxy-4-methoxyphenyl)-2-(methylsulfonyl)ethyl)-1,3-dioxo isoindolin-4-yl)amino)-2-oxoethyl 2,2-dimethyl-3-(nitrooxy)propanoate, also referred to as "compound-1", which has the following structure:

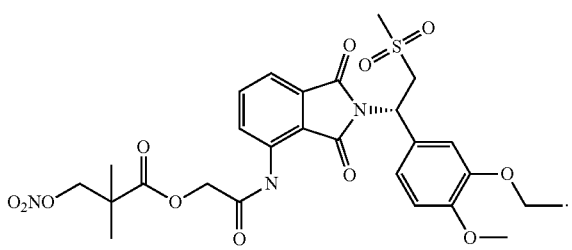

In some embodiments, the compound may be (S)-2-((2-(1-(3-ethoxy-4-methoxyphenyl)-2-(methylsulfonyl)ethyl)-1,3-dioxoisoindolin-4-yl)amino)-2-oxoethyl 2-methyl-3-(nitrooxy)-2-((nitrooxy)methyl)propanoate, also referred to as "compound-2", which as the following structure:

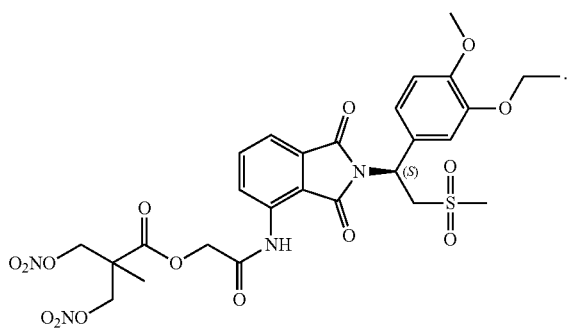

In some embodiments, the compound may be (S)-3-((2-((2-(1-(3-ethoxy-4-methoxyphenyl)-2-(methylsulfonyl)ethyl)-1,3-dioxoisoindolin-4-yl)amino)-2-oxoethyl)amino)-2,2-dimethyl-3-oxopropyl nitrate, also referred to as "compound-3", which has the following structure:

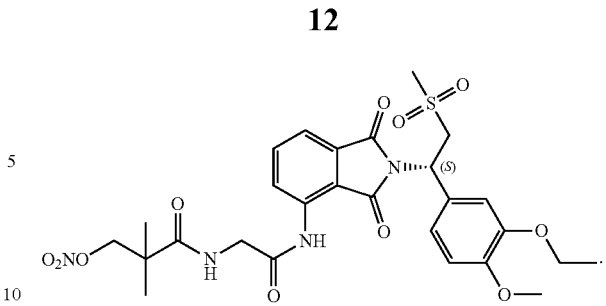

In some embodiments, the compound may be (3R,3aS,6S,6aR)-6-(2-((2-((S)-1-(3-ethoxy-4-methoxyphenyl)-2-(methylsulfonyl)ethyl)-1,3-dioxoisoindolin-4-yl)amino)-2-oxoethoxy)hexahydrofuro[3,2-b]furan-3-yl nitrate, also referred to as "compound-4", which has the following structure:

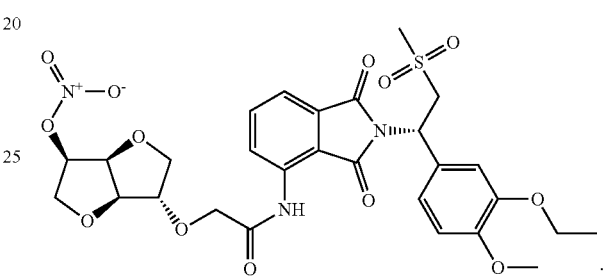

In some embodiments, the compound may be (3S,3aR,6R,6aS)-6-(nitrooxy)hexahydrofuro[3,2-b]furan-3-yl (2-((2-((S)-1-(3-ethoxy-4-methoxyphenyl)-2-(methylsulfonyl)ethyl)-1,3-dioxoisoindolin-4-yl)amino)-2-oxoethyl) carbamate, also referred to as "compound-5", which has the following structure:

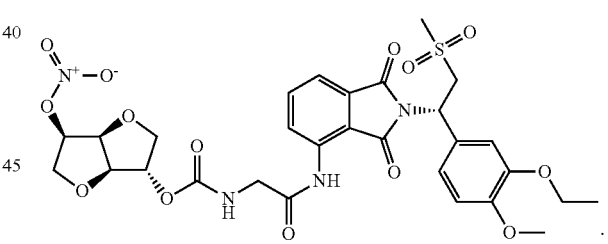

Figure 3:
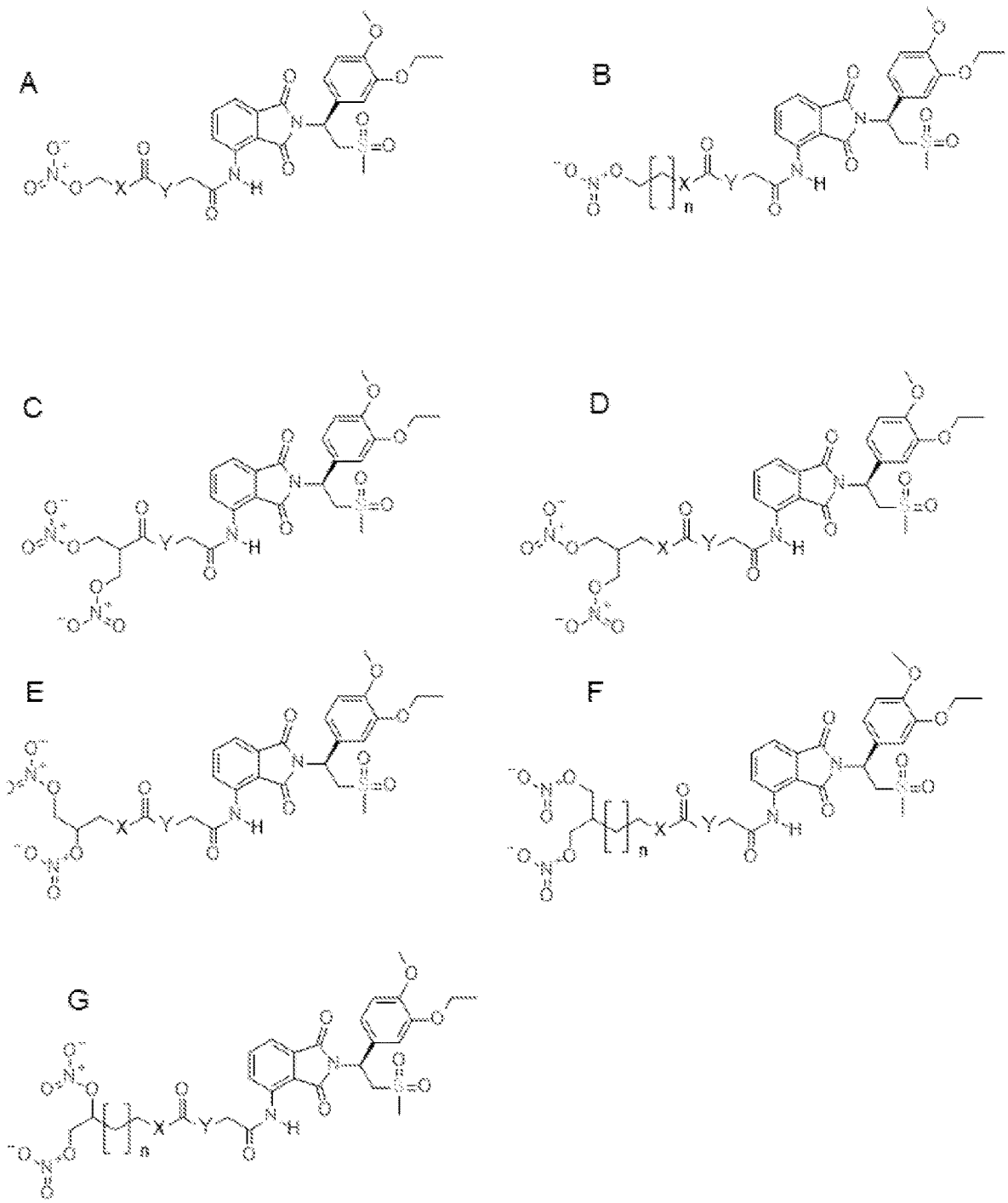
FIG. 3 is a diagram illustrating some exemplary formulas of novel NO-releasing PDE4 inhibitors according to some embodiments of the present disclosure.

FIG. 3 is a diagram illustrating some exemplary formulas of novel NO-releasing PDE4 inhibitors according to some embodiments of the present disclosure. In some embodiments, X shown in FIG. 3 may be O, S, or $CH_2$, etc. In some embodiments, n may range from 1 to 20. In some embodiments, Y shown in FIG. 3 may be O, N, S, or $CH_2$, etc. For example, X can be $CH_2$ and Y can be N. As another example, X can be $CH_2$ and Y can be O. Compounds A-G shown in FIG. 3 have both a NO releasing property and a PDE4 inhibition property. For example, compound D includes two —$ONO_2$ groups. A compound D molecule may release two NO molecules via bioactivation. Merely by way of example, compounds A-G may be used for treating or preventing virus or bacteria infection, vasculature injury related diseases, psoriasis, psoriatic arthritis, or other immune system related inflammatory diseases.

Figure 4:
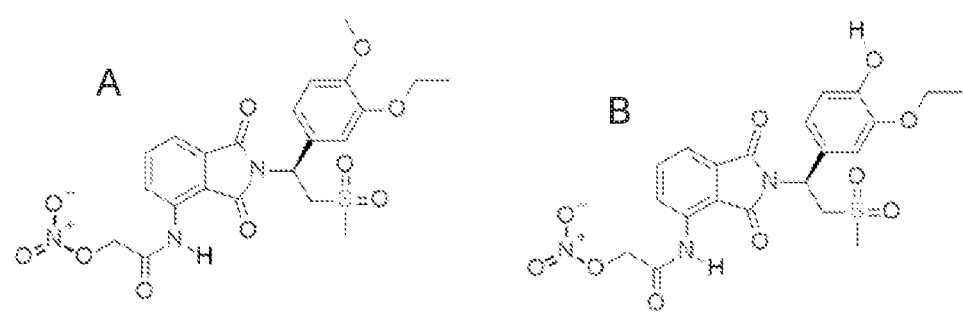
FIG. 4 is a diagram illustrating some exemplary novel NO-releasing PDE4 inhibitors according to some embodiments of the present disclosure.

FIG. 4 is a diagram illustrating some exemplary novel NO-releasing PDE4 inhibitors according to some embodiments of the present disclosure. Merely by way of example, compounds A and B may be used for treating or preventing virus or bacteria infection, vasculature injury related diseases, psoriasis, psoriatic arthritis, or other immune system related inflammatory diseases.

According to another aspect of the present disclosure, a use of the fore-mentioned compound is provided. The compound may be used for the treatment or prevention of some human diseases or animal diseases. In some embodiments, the present invention is directed to a use of a compound of the present disclosure for the preparation of a medicament for the treatment or prevention of certain human or animal diseases, as herein disclosed, or as related to the mechanisms and functions of the compound herein disclosed.

In some embodiments, these compounds may be configured to treat PDE-related diseases. In some embodiments, these compounds may be configured to treat a PDE-related disease with a larger therapeutic window than the PDE inhibitor itself (which includes the functional group in $L_2$ that is capable of inhibiting PDE). As used herein, the term "therapeutic window" refers to a range of drug dosages which can treat a disease effectively without causing unwanted adverse responses such as toxic effects, or causing toxic effects that are lower than a predetermined toxic effect level.

In some embodiments, the PDE related disease may include a PDE4-related disease. Specifically, the PDE4-related disease may include but not limited to a PDE4A-related disease, a PDE4B-related disease, a PDE4C-related disease, or a PDE4D-related disease. In some embodiments, the compound may exhibit a half maximal inhibitory concentration (IC50) of less than 720 nM for inhibiting PDE4A.

In some embodiments, the compound may exhibit an IC50 of less than 200 nM for inhibiting PDE4A. In some embodiments, the compound may exhibit an IC50 of less than 2.3 μM for inhibiting PDE4C. In some embodiments, the compound may exhibit an IC50 of less than 0.7 μM for inhibiting PDE4C.

For example, the compound may be compound-2, and may exhibit an IC50 of less than 320 nM, less than 315 nM, or less than 310 nM for inhibiting PDE4A. The compound-2 may exhibit an IC50 of less than 2.5 μM, less than 2.3 μM, or less than 2.275 μM for inhibiting PDE4C. As another example, the compound may be compound-1, and may exhibit an IC50 of less than 200 nM, less than 190 nM, or less than 180 nM for inhibiting PDE4A. The compound-1 may exhibit an IC50 of less than 2.5 μM, less than 2.3 μM, or less than 2.24 μM for inhibiting PDE4C. As yet another example, the compound may be compound-3. The compound-3 may exhibit an IC50 of less than 250 nM, less than 230 nM, or less than 220 nM for inhibiting PDE4A. The compound-3 may exhibit an IC50 of less than 1.2 μM or less than 1.1 μM for inhibiting PDE4C. As still another example, the compound may be compound-4. The compound-4 may exhibit an IC50 of less than 750 nM, less than 730 nM, or less than 720 nM for inhibiting PDE4A. The compound-4 may exhibit an IC50 of less than 300 nM, less than 150 nM, or less than 120 nM for inhibiting PDE4C. As yet another example, the compound may be compound-5. The compound-5 may exhibit an IC50 of less than 100 nM, less than 80 nM, or less than 45 nM for inhibiting PDE4A. The compound-5 may exhibit an IC50 of less than 1000 nM, less than 900 nM, or less than 850 nM for inhibiting PDE4A.

In some embodiments, the compound may be further configured to improve microcirculation, reduce inflammation, improve immune regulation, or stimulate endothelium damage repair.

In some embodiments, the compound may be further configured to improve microcirculation, reduce inflammation, improve immune regulation, and stimulate endothelium damage repair simultaneously for treating related disorders in the subject.

In some embodiments, the compound may be further configured to release NO and inhibit the activity of the PDE in local tissues when administered to the subject. For example, after the compound is administered to the subject, a level of plasma nitrate in the subject may be increased.

In some embodiments, the compound may be further configured to enhance PDE4 inhibition to the vasculature and sub-vasculature space for enhanced therapeutic windows to treat related diseases.

In some embodiments, the compound may be further configured to treat inflammatory, immunological, or vasculature disorders.

In some embodiments, the compound may be further configured to possess/use a tunable NO releasing property. In some embodiments, the tunable NO releasing property may be used to modulate the delivery of PDE4 inhibitor into the vasculature/near vasculature space. The NO releasing property of the compound may be modulated by modifying the count of NO releasing groups in $L_1$ of the compound. For example, by increasing the count of NO releasing groups in $L_1$ of the compound, the compound may be able to release more NO molecules, thus increasing the concentration of NO in local tissue. Additionally, or alternatively, by increasing the count of NO releasing groups in $L_1$ of the compound, the compound may be able to continuously release NO for a longer time.

According to yet another aspect of the present disclosure, a method of treating or preventing diseases or disorders is provided. The method may include administering to the subject a pharmaceutically effective amount of the aforementioned compound. For example, the method may include administering the composition to the subject via an oral administration, an injection administration, a topical administration, or the like, or any combination thereof.

According to still another aspect of the present disclosure, a composition including the compound may be formulated and used for treating or preventing diseases or disorders. In some embodiments, the pharmaceutical composition may further include an excipient.

In some embodiments, the composition may further include a pharmaceutically acceptable carrier. For instance, the carrier may include a coating layer, a capsule, a microcapsule, a nanocapsule, or the like, or any combination thereof. It should be noted that the carrier may need to be non-toxic and may not have significant impacts on the activity of the key ingredients in the pharmaceutical composition (e.g., the compound described above). In some embodiments, the carrier may provide protection for the key ingredients against some undesired conditions, such as oxidation, the decomposition or inactivation of the key ingredients. For instance, enzymes or relatively low-pH in the stomach may cause the decomposition or inactivation of the key ingredients. The carrier may help maintain or increase the efficacy of the pharmaceutical composition by protecting the key ingredients in the pharmaceutical composition. In some embodiments, the carrier may be used for controlled release of the key ingredients. The controlled release may include but is not limited to slow release, sustained release, targeted release, or the like. For instance, the carrier may include hydrogel capsules, microcapsules or nanocapsules made of collagen, gelatin, chitosan, alginate, polyvinyl alcohol, polyethylene oxide, starch, cross-linked starch, or the like, or any combination thereof. In some embodiments, the carrier may facilitate a controlled-release of the key ingredients in the pharmaceutical composition.

In some embodiments, the composition may be formulated as a tablet, a capsule, granules, powder, micelles, liquid, suspension, cream, foam, gels, lotion, pastes, or ointment.

In some embodiments, the composition may be administered to the subject via an oral administration, an injection administration, or a topical administration. In some embodiments, the injection administration may include subcutaneous injection, intramuscular injection, intravenous injection, or the like. In some embodiments, the injection administration may include injection of the composition into a tumor or a region close to the tumor. In some embodiments, the injection administration may include injection of the composition into the kidney, liver, heart, thyroid or joints. In some embodiments, the topical administration may include applying the composition on the skin to attenuate cancer such as skin cancer, lymphoma. In some embodiments, the topical administration may include vaginal administration, rectal administration, nasal administration, auricular administration, intramedullary administration, intra-articular administration, intra-pleural administration, or the like, or any combination thereof. In some embodiments, the composition may be administered to the subject via a combination of different means of administration. In some embodiments, the method may include administering the composition to the subject three times a day, two times a day, one time a day, once every two days, etc.

In some embodiments, the method may be used for treating or preventing acute lung injury (ALI) or acute respiratory distress syndrome (ARDS) by administering a pharmaceutically effective amount of a compound of the present disclosure to a subject. In some embodiments, the method may be used for treating or preventing ARDS. In some embodiments, the method may be used for treating or preventing ARDS caused by SARS-CoV-2. In some embodiments, the method may be used for treating or preventing ARDS caused by other corona virus infection. In some embodiments, the method may be used for treating or preventing ARDS caused by other virus infection. In some embodiments, the method may be used for treating or preventing ARDS caused by bacteria infection. In some embodiments, the method may be used for treating or preventing ARDS caused by parasite infection. In some embodiments, the method may be used for treating or preventing ARDS caused by fungal infection. In some embodiments, the method may be used for treating or preventing ARDS caused by trauma. In some embodiments, the method may be used for treating or preventing ARDS caused by surgery. In some embodiments, the method may be used for treating or preventing ARDS caused by high attitude airway edema. In some embodiments, the method may be used for treating or preventing ARDS caused by drug induced jury. In some embodiments, the method may be used for treating or preventing ARDS caused by sepsis.

In some embodiments, the method may be used for treating or preventing bronchitis, asthma, chronic obstructive pulmonary disease (COPD), idiopathic pulmonary fibrosis (IPF), high altitude pulmonary edema, or cystic fibrosis by administering a pharmaceutically effective amount of a compound of the present disclosure to a subject.

In some embodiments, the method may be used for improving cytokine storm management by administering a pharmaceutically effective amount of a compound of the present disclosure to a subject. In some embodiments, the method may be used for treating or preventing cytokine storm caused by SARS-CoV-2. In some embodiments, the method may be used for treating or preventing cytokine storm caused by PD-1 or PDI-1 antibody. In some embodiments, the method may be used for treating or preventing cytokine storm caused by therapeutic anti-bodies targeting T-cell, B-cell, neutrophils, macrophages, or monocytes.

In some embodiments, the method may be used for treating or preventing stroke by administering a pharmaceutically effective amount of a compound of the present disclosure to a subject.

In some embodiments, the method may be used for treating or preventing acute kidney injury (AKI), chronic kidney diseases, various types of nephritis, or focal segmental glomerulosclerosis (FSGS), idiopathic FSGS by administering a pharmaceutically effective amount of a compound of the present disclosure to a subject. In some embodiments, the method may be used for treating or preventing AKI caused by cancer drug use.

In some embodiments, the method may be used for treating or preventing nonalcoholic steatohepatitis (NASH), primary biliary cholangitis (PBC), cirrhosis, type 1 diabetes, type 2 diabetes, or diabetes complications by administering a pharmaceutically effective amount of a compound of the present disclosure to a subject. For example, the diabetes complications may include but not limited to diabetic foot, diabetic nerve pain, diabetic neuropathy, diabetic nephropathies, diabetic ketoacidosis, or other diabetic vascular complications.

In some embodiments, the method may be used for treating or preventing allergic reactions or inflammation by administering a pharmaceutically effective amount of a compound of the present disclosure to a subject. In some embodiments, the method may be used for treating or preventing eye diseases including Uveitis, dry eye, eye allergies, macular degeneration (AMD), or glaucoma, by administering a pharmaceutically effective amount of a compound of the present disclosure to a subject.

In some embodiments, the method may be used for treating or preventing peripheral immunological disorders including rheumatoid arthritis (RA), inflammatory bowel disease (IBD), Behcet syndrome, Ulcerative colitis, ankylosing spondylitis, Vulvodynia, Acne, Lichen Planus, Prurigo Nodularis, Discoid Lupus Erythematosus, or Crohn's disease by administering a pharmaceutically effective amount of a compound of the present disclosure to a subject.

In some embodiments, the method may be used for treating or preventing autoimmune diseases including systemic lupus erythematosus (SLE), by administering a pharmaceutically effective amount of a compound of the present disclosure to a subject.

In some embodiments, the method may be used for treating, preventing, or slowing central nervous system diseases, including Alzheimer's disease, Parkinson's disease, or stroke, by administering a pharmaceutically effective amount of a compound of the present disclosure to a subject.

In some embodiments, the method may be used for treating or preventing cancer by administering a pharmaceutically effective amount of a compound of the present disclosure to a subject. For example, the cancer may be leukemia, breast cancer, non-small cell lung cancer, gastric cancer, ovarian cancer, pancreatic cancer, inflammatory breast cancer, prostate cancer, bladder cancer, colon cancer, liver cancer, kidney cancer, or peritoneal cancer. In some embodiments, the leukemia may be acute myelogenous leukemia, acute lymphoblastic leukemia, acute myeloid leukemia, chronic lymphocytic leukemia, or chronic myeloid leukemia.

In some embodiments, the method may be used for treating or preventing multiple sclerosis by administering a pharmaceutically effective amount of a compound of the present disclosure to a subject.

In some embodiments, the method may be used for treating or preventing transplantation rejection by administering a pharmaceutically effective amount of a compound of the present disclosure to a subject.

In some embodiments, the method may be used for treating or preventing sepsis, high altitude pulmonary edema, asthma, or bronchitis by administering a pharmaceutically effective amount of a compound of the present disclosure to a subject.

In some embodiments, the method may be used for treating or preventing allergic rhinitis, diabetes, diabetic neuropathy, allergic conjunctivitis, diabetic macular degeneration, chronic kidney diseases, psoriasis, atopic dermatitis, eosinophilic granuloma, osteoarthritis, colitis, or pancreatitis by administering a pharmaceutically effective amount of a compound of the present disclosure to a subject.

In some embodiments, the method may be used for treating or preventing skin diseases by administering a pharmaceutically effective amount of a compound of the present disclosure to a subject. For example, the skin diseases may include psoriasis, atopic dermatitis, eosinophilic granuloma, or psoriasis.

According to some embodiments of the present disclosure, a method of treating or preventing ALI or ARDS is provided. The method may include administering to the subject a pharmaceutically effective amount of some of the aforementioned compounds. For example, the method may include administering one or more of the compounds (e.g., in a composition that includes the one of more compounds and a pharmaceutically acceptable carrier) to the subject to treat ARDS via an oral administration, an injection administration, a topical administration, or the like, or any combination thereof. In some embodiments, the compound is compound-1, compound-2, compound-3, compound-4, or compound-5.

According to some embodiments of the present disclosure, a method of treating or preventing a PDE-related disease in a subject is provided. For example, the PDE-related disease may include a PDE4-related disease, such as a PDE4A-related disease, a PDE4B-related disease, a PDE4C-related disease, or a PDE4D-related disease, or the like, or any combination thereof. In some embodiments, the method may include administering one or more of the compounds (e.g., in a composition that includes the one of more compounds and a pharmaceutically acceptable carrier) to the subject to treat ARDS via an oral administration, an injection administration, a topical administration, or the like, or any combination thereof. In some embodiments, the compound is compound-1, compound-2, compound-3, compound-4, or compound-5.

Merely by way of example, the method for treating or preventing ALI, ARDS, or the PDE-related disease may include orally administering the compound to the subject at 0.01-50 mg/kg. As another example, the method may include orally administering the compound to the subject at 1-50 mg/kg. As yet another example, the method may include orally administering the compound to the subject at 5-50 mg/kg. In some embodiments, the method may include orally administering compound-1, compound-2, compound-3, compound-4, or compound-5, or any combination thereof, to the subject at about 5 mg/kg, 10 mg/kg, or 50 mg/kg.

In some embodiments, a use of some of the aforementioned compounds for treating or preventing ALI or ARDS is provided. For example, the compounds may include one or more of compound-1, compound-2, compound-3, compound-4, or compound-5.

According to some embodiments of the present disclosure, a use of some of the aforementioned compounds for treating or preventing cancer is provided. For example, the compounds may include one or more of compound-1, compound-2, compound-3, compound-4, or compound-5.

According to some embodiments of the present disclosure, a use of some of the aforementioned compounds for treating or preventing a PDE-related disease is provided. For example, the compounds may include one or more of compound-1, compound-2, compound-3, compound-4, or compound-5.

In some embodiments, the composition including the compound may be administered to the subject before or after the administration of other pharmaceutical compositions for treating a disease or disorder. Alternatively, the composition and other pharmaceutical compositions may be administered to the subject simultaneously for treating the disease or disorder.

The present disclosure is further described according to the following examples, which should not be construed as limiting the scope of the present disclosure.

EXAMPLES

Example 1—Preparation of (S)-2-((2-(1-(3-Ethoxy-4-Methoxyphenyl)-2-(Methylsulfonyl)Ethyl)-1,3-Dioxo Isoindolin-4-Yl)Amino)-2-Oxoethyl 2,2-Dimethyl-3-(Nitrooxy)Propanoate (Also Referred to as Compound-1)

Figure 5:
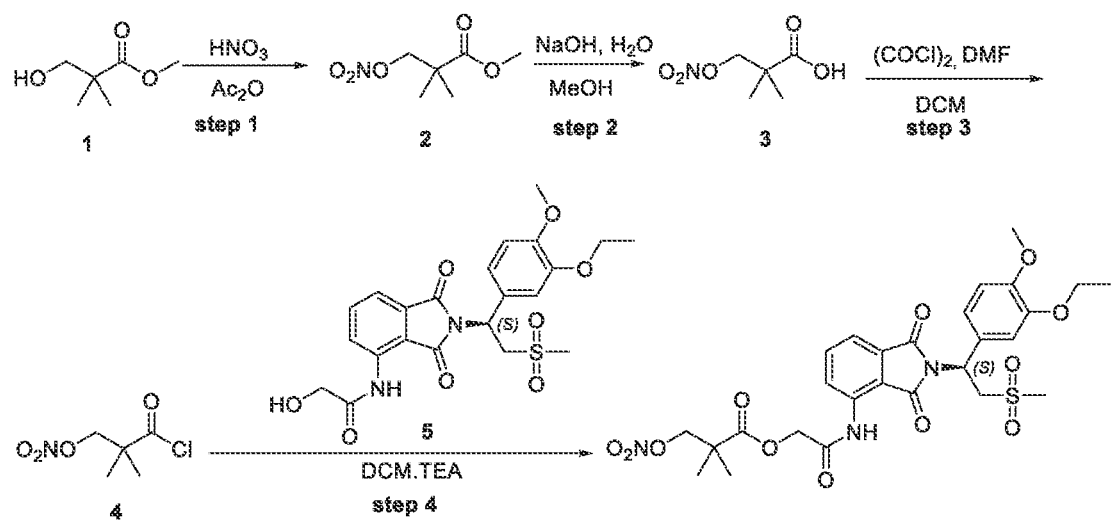
FIG. 5 is a diagram illustrating an exemplary process of preparing compound-1 according to some embodiments of the present disclosure.

Compound-1 was prepared as the following steps. FIG. 5 is a diagram illustrating an exemplary process of preparing compound-1 according to some embodiments of the present disclosure.

Step 1, methyl 2,2-dimethyl-3-(nitrooxy)propanoate (also referred to as product 2 illustrated in FIG. 5) was prepared as follows:

$HNO_3$ (0.2 mL) was added successively to a solution of methyl 3-hydroxy-2,2-dimethylpropanoate (2 mL) in acetic anhydride (10 mL). The reaction mixture was stirred under nitrogen at 0° C. for 2 hours (hrs). Water (20 mL) was added and the mixture was extracted with EA (20 mL×2). The combined organic layers were washed with saturated $NaHCO_3$ solution (20 mL×2) and saturated brine (20 mL×2), dried over $Na_2SO_4$. Then the resultant was filtered to collect the filtrate. The filtrate was concentrated to afford product 2 (2.2 g, 84% yield) as light yellow oil. NMR spectrometry was conducted on the resultant compound, and the test results are as follows: 1H NMR (300 MHz, CDCl3) δ 4.49 (s, 2H), 3.71 (s, 3H), 1.46-1.10 (m, 6H).

Step 2, 2,2-dimethyl-3-(nitrooxy)propanoic acid (also referred to as product 3 illustrated in FIG. 5) was prepared as follows:

To a solution of methyl 2,2-dimethyl-3-(nitrooxy)propanoate (2.2 g, 0.012 mol) in MeOH (20 mL) was added NaOH (2.5 M, 20 mL). The solution was stirred under nitrogen at rt for 16 hrs. MeOH was removed under vacuum. Water (30 mL) was added, acidified to pH 3-4 with 5 N aqueous HCl, extracted with EA (30 mL×3). The organic layer was washed with brine (30 mL), concentrated to dryness to give the product 3 (2 g, 89% yield) as a light yellow oil. NMR spectrometry was conducted on the resultant compound, and the test results are as follows: 1H NMR (300 MHz, CDCl3) δ 11.04 (s, 1H), 4.48 (d, J=19.8 Hz, 2H), 1.40-1.28 (m, 6H).

Step 3, 3-chloro-2,2-dimethyl-3-oxopropyl nitrate (also referred to as product 4 as illustrated in FIG. 5) was prepared as follows:

To a solution of 2,2-dimethyl-3-(nitrooxy)propanoic acid (200 mg, 1.23 mmol) in DCM (10 mL) was added oxalyl chloride (0.17 mL, 1.84 mmol), 0.05 mL of dimethyl formamide (DMF). After 2 hours, the solution was concentrated under reduced pressure and the crude product was extracted with EA (20 mL×3). The organic layer was washed with brine (20 mL), concentrated to dryness to give the product 4 (200 mg, 90% yield) as a light yellow oil.

Step 4, (S)-2-((2-(1-(3-ethoxy-4-methoxyphenyl)-2-(methylsulfonyl)ethyl)-1,3-dioxoisoindolin-4-yl)amino)-2-oxoethyl 2,2-dimethyl-3-(nitrooxy)propanoate (compound-1) was prepared as follows:

To a solution of 3-chloro-2,2-dimethyl-3-oxopropyl nitrate (150 mg, 0.83 nmol) and TEA (251 mg, 2.47 mmol) in dichloromethane (DCM) (10 mL) was added a solution of N-{2-[(1S)-1-(3-ethoxy-4-methoxyphenyl)-2-methanesulfonylethyl]-1,3-dioxoisoindol-4-yl}-2-hydroxyacetamide (also referred to as compound-6) in DCM. The solution was stirred under nitrogen at rt for 1 h. Water (20 mL) was added and the mixture was extracted with DCM (20 mL×2). The combined organic layers were washed with saturated brine (20 mL×2), dried over $Na_2SO_4$. Then the resultant was filtered to collect the filtrate. The filtrate was concentrated. The crude product was purified by silica gel column chromatography (PE/EA=1:1) to afford compound-1 (90 mg, 17% yield) as a light yellow solid. Mass and NMR spectrometry was conducted on the resultant compound, and the test results are as follows: Mass (m/z): 643.9 [M+Na]$^+$. $^1$H NMR (400 MHz, DMSO-d$^6$) δ 10.04 (s, 1H), 8.53 (d, J=8.4 Hz, 1H), 7.82 (t, J=7.8 Hz, 1H), 7.61 (d, J=7.4 Hz, 1H), 7.07 (s, 1H), 7.00 (d, J=8.4 Hz, 1H), 6.93 (d, J=8.4 Hz, 1H), 5.77 (dd, J=11.2, 4.8 Hz, 1H), 4.85 (s, 2H), 4.74 (s, 2H), 4.32 (dd, J=14.0, 10.8 Hz, 1H), 4.15 (dd, J=14.2, 4.2 Hz, 1H), 4.01 (q, J=6.8 Hz, 2H), 3.73 (s, 3H), 3.01 (s, 3H), 1.35-1.31 (m, 9H).

Example 2—Preparation of (({2-[(1S)-1-(3-Ethoxy-4-Methoxyphenyl)-2-Methanesulfonylethyl]-1,3-Dioxoisoindol-4-Yl}Carbamoyl)Methyl 2-Methyl-3-(Nitrooxy)-2-[(Nitrooxy) Methyl]Propanoate (Also Referred to as Compound-2)

Figure 6:
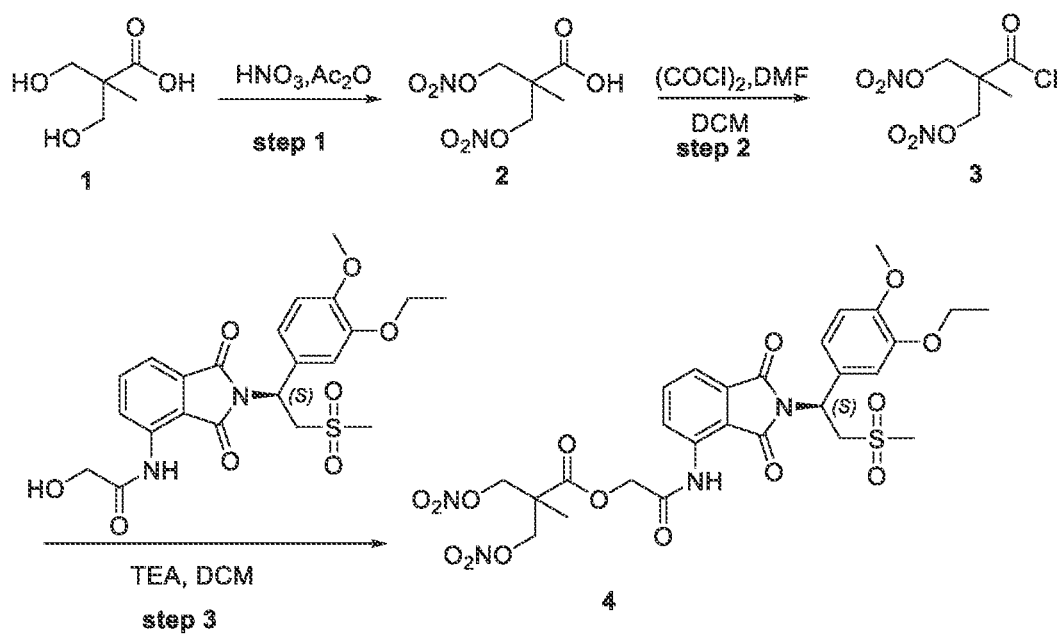
FIG. 6 is a diagram illustrating an exemplary process of preparing compound-2 according to some embodiments of the present disclosure.

Compound-2 was prepared as the following steps. FIG. 6 is a diagram illustrating an exemplary process of preparing compound-2 according to some embodiments of the present disclosure.

Step 1, 2-methyl-3-(nitrooxy)-2-[(nitrooxy)methyl]propanoic acid (also referred to as product 2 illustrated in FIG. 6) was prepared as follows:

$HNO_3$ (0.5 mL) were added successively to a solution of 3-hydroxy-2-(hydroxymethyl)-2-methylpropanoic acid (2 mL) in acetic anhydride (20 mL). The reaction mixture was stirred under nitrogen at rt for 2 hrs. Water (20 mL) was added and the mixture was extracted with EA (20 mL×2). The combined organic layers were washed with saturated $NaHCO_3$ solution (20 mL×2) and saturated brine (20 mL×2), dried over $Na_2SO_4$. Then the resultant was filtered to collect the filtrate. The filtrate was concentrated to afford compound-2 (2.9 g, 50% yield) as a light yellow oil. NMR spectrometry was conducted on the resultant compound, and the test results are as follows: $^1$H NMR (400 MHz, DMSO) δ 13.41 (s, 1H), 4.68 (d, J=2.0 Hz, 4H), 1.32-1.21 (m, 3H).

Step 2, 2-methyl-3-(nitrooxy)-2-[(nitrooxy)methyl]propanoyl chloride was prepared as follows:

To a solution of 2-methyl-3-(nitrooxy)-2-[(nitrooxy)methyl]propanoic acid (500 mg, 2.23 mmol) in DCM (15 mL) was added oxalyl chloride (0.43 mL, 3.34 mmol), 0.1 mL of DMF. After 2 hours, the solution was concentrated under reduced pressure and the crude product was extracted with EA (20 mL×3). The organic layer was washed with brine (20 mL), concentrated to dryness to give the product 4 (500 mg, 74% yield) as a light yellow oil.

Step 3, (S)-2-((2-(1-(3-ethoxy-4-methoxyphenyl)-2-(methylsulfonyl) ethyl)-1,3-dioxoisoindolin-4-yl)amino)-2-oxoethyl 2,2-dimethyl-3-(nitrooxy) propanoate (compound-2) was prepared as follows:

To a solution of 2-methyl-3-(nitrooxy)-2-[(nitrooxy)methyl]propanoyl chloride (210 mg, 0.87 mmol) and TEA (251 mg, 2.47 mmol) in DCM (10 mL) was added a solution of N-{2-[(1S)-1-(3-ethoxy-4-methoxyphenyl)-2-methanesulfonylethyl]-1,3-dioxoisoindol-4-yl}-2-hydroxyacetamide (500 mg, 1.05 mmol) in DCM (2 mL). The reaction mixture was stirred under nitrogen at rt for 1 h. Water (20 mL) was added and the mixture was extracted with DCM (20 mL×2). The combined organic layers were washed with saturated brine (20 mL×2), dried over $Na_2SO_4$. Then the resultant was filtered to collect the filtrate. The filtrate was concentrated. The crude product was purified by silica gel column chromatography (PE/EA=2:1) to afford compound 2 (400 mg, 67% yield) as a light yellow solid. Mass and NMR spectrometry was conducted on the resultant compound, and the test results are as follows: Mass (m/z): 704.8 [M+Na]$^+$. $^1$HNMR (400 MHz, DMSO-d$^6$) 610.07 (s, 1H), 8.51 (d, J=8.4 Hz, 1H), 7.84 (t, J=7.8 Hz, 1H), 7.63 (d, J=7.2 Hz, 1H), 7.07 (d, J=1.8 Hz, 1H), 7.00 (dd, J=8.4, 1.8 Hz, 1H), 6.94 (d, J=8.4 Hz, 1H), 5.77 (dd, J=11.2, 3.2 Hz, 1H), 4.92 (d, J=0.5 Hz, 2H), 4.87 (d, J=4.2 Hz, 4H), 4.33 (dd, J=14.2, 10.8 Hz, 1H), 4.15 (dd, J=14.4, 4.2 Hz, 1H), 4.07-3.97 (m, 2H), 3.74 (s, 3H), 3.01 (s, 3H), 1.44 (s, 3H), 1.33 (t, J=7.0 Hz, 3H).

Example 3—Preparation of (S)-3-((2-((2-(1-(3-Ethoxy-4-Methoxyphenyl)-2-(Methylsulfonyl) Ethyl)-1,3-Dioxoisoindolin-4-Yl)Amino)-2-Oxoethyl)Amino)-2,2-Dimethyl-3-Oxopropyl Nitrate (Also Referred to as Compound-3)

Figure 7:
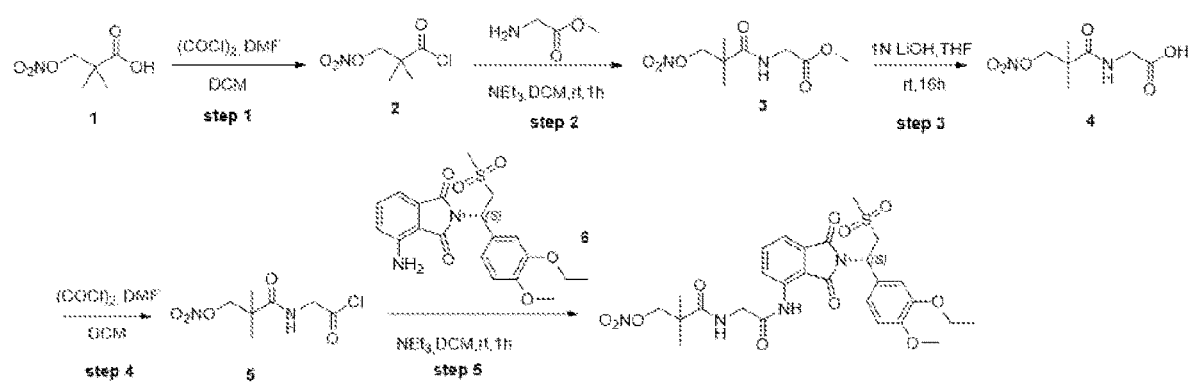
FIG. 7 is a diagram illustrating an exemplary process of preparing compound-3 according to some embodiments of the present disclosure.

Compound-3 was prepared as the following steps. FIG. 7 is a diagram illustrating an exemplary process of preparing compound-3 according to some embodiments of the present disclosure.

Step 1, 3-chloro-2,2-dimethyl-3-oxopropyl nitrate was prepared as follows:

To a solution of 2,2-dimethyl-3-(nitrooxy)propanoic acid (318 mg, 1.95 mmol) in DCM (10 mL) were added (COCl)$_2$ (297 mg, 2.34 mmol) and DMF (50 mg). The mixture was stirred at rt for 1 hr, and then concentrated to afford 3-chloro-2,2-dimethyl-3-oxopropyl nitrate (0.4 g, 99% yield) as a white solid, which is used in the next step directly.

Step 2, methyl (2,2-dimethyl-3-(nitrooxy)propanoyl) glycinate was prepared as follows:

To a solution of 3-chloro-2,2-dimethyl-3-oxopropyl nitrate (0.4 g, 1.95 mmol) in DCM (20 mL) were added methyl glycinate. HCl (295 mg, 2.34 mmol) and triethylamine (591 mg, 5.85 mmol). The solution was stirred at rt for 2 h. Water (30 mL) was added and the mixture was extracted with DCM (20 mL×3). The combined organic layers were washed with brine (20 mL×3), dried over Na₂SO₄. Then the resultant was filtered to collect the filtrate. The filtrate was concentrated. The crude product was purified by Flash Chromatography (PE/EA=2:1) to afford methyl (2,2-dimethyl-3-(nitrooxy)propanoyl)glycinate (0.384 g, 84% yield) as a colorless oil.

Step 3, (2,2-dimethyl-3-(nitrooxy)propanoyl)glycine was prepared as follows:

To a solution of methyl (2,2-dimethyl-3-(nitrooxy)propanoyl)glycinate (0.384 g, 1.64 mmol) in THF (10 mL) were added H₂O (6 mL) and LiOH (157 mg, 6.56 mmol). The solution was stirred at rt for 16 h. 1 N HCl was used to adjust the pH=2-3, Water (30 mL) was added and the mixture was extracted with EA (20 mL×3). The combined organic layers were washed with brine (20 mL×3), dried over Na₂SO₄. Then the resultant was filtered to collect the filtrate. The filtrate was concentrated to afford (2,2-dimethyl-3-(nitrooxy)propanoyl)glycine (0.4 g, 99% yield) as a yellow oil. Mass spectrometry was conducted on the resultant compound, and the test results are as follows: Mass (m/z): 439.1 [2M−H]⁺.

Step 4, 3-chloro-2,2-dimethyl-3-oxopropyl nitrate was prepared as follows:

To a solution of (2,2-dimethyl-3-(nitrooxy)propanoyl) glycine (0.4 g, 1.64 mmol) in DCM (10 mL) were added (COCl)₂ (352 mg, 2.77 mmol) and DMF (50 mg). The mixture was stirred at rt for 1 hr, and then concentrated to afford 3-chloro-2,2-dimethyl-3-oxopropyl nitrate (0.5 g, 99% yield) as a white oil, which is used in the next step directly.

Step 5, (S)-3-((2-((2-(1-(3-ethoxy-4-methoxyphenyl)-2-(methylsulfonyl)ethyl)-1,3-dioxoisoindolin-4-yl)amino)-2-oxoethyl)amino)-2,2-dimethyl-3-oxopropyl nitrate was prepared as follows:

To a solution of 3-chloro-2,2-dimethyl-3-oxopropyl nitrate (0.5 g, 1.64 mmol) in DCM (20 mL) were added (S)-4-amino-2-(1-(3-ethoxy-4-methoxyphenyl)-2-(methylsulfonyl)ethyl)isoindoline-1,3-dione (330 mg, 0.79 mmol) and triethylamine (591 mg, 5.85 mmol). The solution was stirred at rt for 2 h. Water (30 mL) was added and the mixture was extracted with DCM (20 mL×3). The combined organic layers were washed with brine (20 mL×3), dried over Na₂SO₄. Then the resultant was filtered to collect the filtrate. The filtrate was concentrated. The crude product was purified by Flash Chromatography (PE/EA=1:1) to afford (S)-3-((2-((2-(1-(3-ethoxy-4-methoxyphenyl)-2-(methylsulfonyl)ethyl)-1,3-dioxoisoindolin-4-yl)amino)-2-oxoethyl)amino)-2,2-dimethyl-3-oxopropyl nitrate (144 mg, 14% yield) as a yellow solid. Mass spectrometry was conducted on the resultant compound, and the test results are as follows: Mass (m/z): 621.2 [M+H]⁺.

Example 4—Preparation of (3R,3aS,6S,6aR)-6-(2-((2-((S)-1-(3-Ethoxy-4-Methoxyphenyl)-2-(Methylsulfonyl)Ethyl)-1,3-Dioxoisoindolin-4-Yl)Amino)-2-Oxoethoxy)Hexahydrofuro[3,2-b]Furan-3-Yl Nitrate (Also Referred to as Compound-4)

Figure 8:
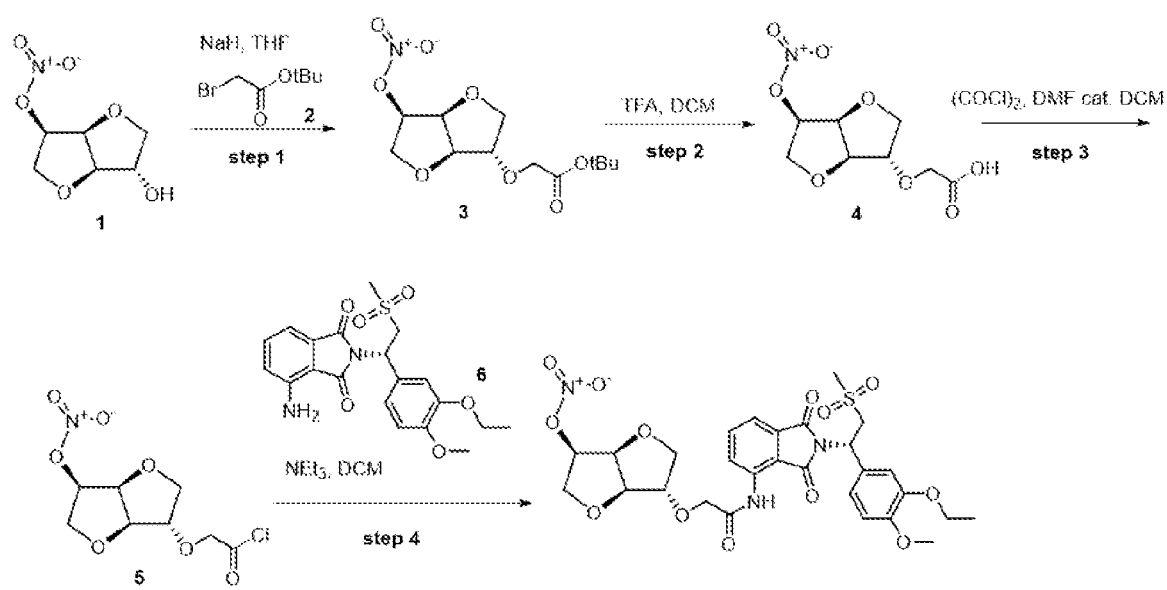
FIG. 8 is a diagram illustrating an exemplary process of preparing compound-4 according to some embodiments of the present disclosure.

Compound-4 was prepared as the following steps. FIG. 8 is a diagram illustrating an exemplary process of preparing compound-4 according to some embodiments of the present disclosure.

Step 1, Preparation of tert-butyl 2-(((3S,3aR,6R,6aS)-6-(nitrooxy)hexahydrofuro[3,2-b]furan-3-yl)oxy)acetate was prepared as follows:

To a solution of (3R,3aS,6S,6aR)-6-hydroxyhexahydrofuro[3,2-b]furan-3-yl nitrate (1 g, 5.24 mmol) in THF (60 mL) was added NaH (60%, 230 mg, 5.76 mmol), and the mixture was stirred at rt for 1 hr. Tert-butyl 2-bromoacetate (1.12 g, 5.76 mmol) was added to the mixture. The mixture was further stirred at rt for 16 hrs. Water (30 mL) was added and the mixture was extracted with EA (30 mL×3). The combined organic layers were washed with brine (20 mL×2), dried over Na₂SO₄. Then the resultant was filtered to collect the filtrate. The filtrate was concentrated. The crude product was purified by Flash Chromatography (PE/EA=4:1) to afford tert-butyl 2-(((3S,3aR,6R,6aS)-6-(nitrooxy)hexahydrofuro[3,2-b]furan-3-yl)oxy)acetate (0.8 g, 50% yield) as a light-yellow oil.

Step 2, 2-(((3S,3aR,6R,6aS)-6-(nitrooxy)hexahydrofuro [3,2-b]furan-3-yl)oxy)acetic acid was prepared as follows:

To a solution of tert-butyl 2-(((3S,3aR,6R,6aS)-6-(nitrooxy)hexahydrofuro[3,2-b]furan-3-yl)oxy)acetate (0.8 g, 2.62 mmol) in DCM (10 mL) was added TFA (3 mL). The mixture was stirred at rt for 16 hrs and concentrated to afford 2-(((3S,3aR,6R,6aS)-6-(nitrooxy)hexahydrofuro[3,2-b] furan-3-yl)oxy)acetic acid (0.9 g, 99% yield) as a light-yellow oil.

Step 3, (3R,3aS,6S,6aR)-6-(2-chloro-2-oxoethoxy)hexahydrofuro[3,2-b]furan-3-yl nitrate was prepared as follows:

To a solution of 2-(((3S,3aR,6R,6aS)-6-(nitrooxy)hexahydrofuro[3,2-b]furan-3-yl)oxy)acetic acid (0.9 g, 2.62 mmol) in DCM (10 mL) were added (COCl)₂ (0.4 g, 3.12 mmol) and DMF (50 mg). The mixture was stirred at rt for 1 hr. Concentrated to afford (3R,3aS,6S,6aR)-6-(2-chloro-2-oxoethoxy)hexahydrofuro[3,2-b]furan-3-yl nitrate (1.0 g, 99% yield) as a light-yellow oil. Used in the next step directly.

Step 4, Preparation of (3R,3aS,6S,6aR)-6-(2-((2-((S)-1-(3-ethoxy-4-methoxyphenyl)-2-(methylsulfonyl)ethyl)-1,3-dioxoisoindolin-4-yl)amino)-2-oxoethoxy)hexahydrofuro [3,2-b]furan-3-yl nitrate was prepared as follows:

To a solution of (3R,3aS,6S,6aR)-6-(2-chloro-2-oxoethoxy)hexahydrofuro[3,2-b]furan-3-yl nitrate (1.0 g, 2.62 mmol) in DCM (20 mL) were added (S)-4-amino-2-(1-(3-ethoxy-4-methoxyphenyl)-2-(methylsulfonyl)ethyl)isoindoline-1,3-dione (125 mg, 0.299 mmol) and triethylamine (1.32 g, 13.1 mmol). The solution was stirred at rt for 2 h. Water (30 mL) was added and the mixture was extracted with DCM (20 mL×3). The combined organic layers were washed with brine (20 mL×3), dried over Na₂SO₄. Then the resultant was filtered to collect the filtrate. The filtrate was concentrated. The crude product was purified by prep-HPLC (ACN—H₂O, 0.1% FA) to afford (3R,3aS,6S,6aR)-6-(2-((2-((S)-1-(3-ethoxy-4-methoxyphenyl)-2-(methylsulfonyl) ethyl)-1,3-dioxoisoindolin-4-yl)amino)-2-oxoethoxy)hexahydrofuro[3,2-b]furan-3-yl nitrate (20 mg, 10% yield) as a white solid. Mass spectrometry was conducted on the resultant compound, and the test results are as follows: Mass (m/z): 650.2 [M+H]⁺.

Example 5—Preparation of (3S,3aR,6R,6aS)-6-(Nitrooxy)Hexahydrofuro[3,2-b]Furan-3-Yl (2-((2-((S)-1-(3-Ethoxy-4-Methoxyphenyl)-2-(Methylsulfonyl)Ethyl)-1,3-Dioxoisoindolin-4-Yl)Amino)-2-Oxoethyl)Carbamate (Compound-5)

Figure 9:
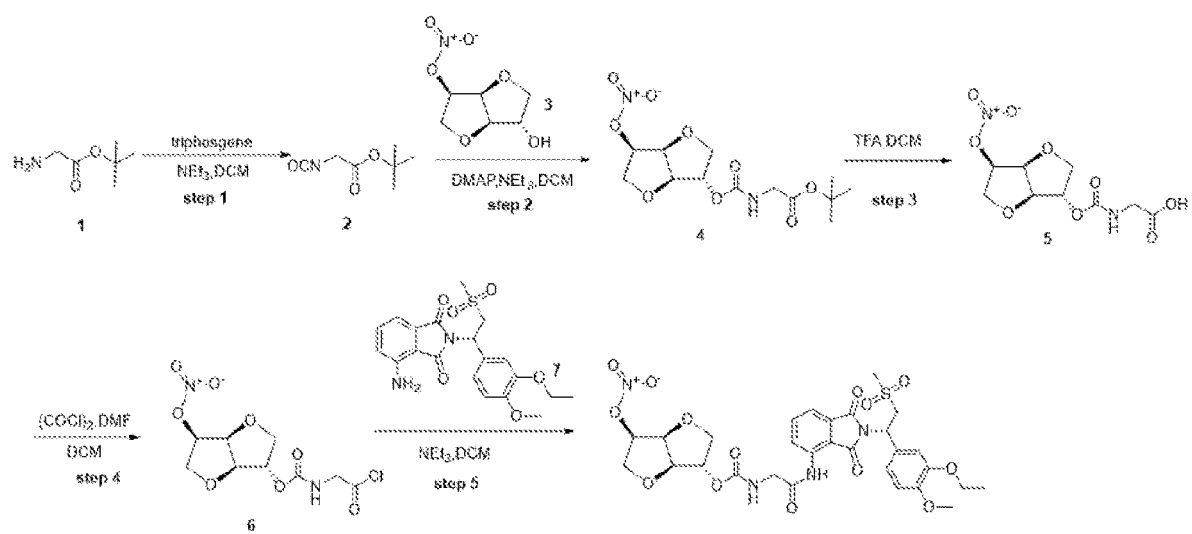
FIG. 9 is a diagram illustrating an exemplary process of preparing compound-5 according to some embodiments of the present disclosure.

Compound-5 was prepared as the following steps. FIG. 9 is a diagram illustrating an exemplary process of preparing compound-5 according to some embodiments of the present disclosure.

Step 1, tert-butyl 2-isocyanatoacetate was prepared as follows:

To a solution of tert-butyl glycinate (300 mg, 2.29 mmol) in DCM (20 mL) were added triphosgene (238 mg, 0.80 mmol) and NEt3 (692 mg, 6.86 mmol). The mixture was stirred at 0° C. for 1 hr and concentrated to afford tert-butyl 2-isocyanatoacetate (0.4 g, 99% yield) as a light-yellow solid.

Step 2, tert-butyl ((((3S,3aR,6R,6aS)-6-(nitrooxy)hexahydrofuro[3,2-b]furan-3-yl)oxy)carbonyl)glycinate was prepared as follows:

To a solution of tert-butyl 2-isocyanatoacetate (411 mg, 2.62 mmol) in DCM (30 mL) were added (3R,3aS,6S,6aR)-6-hydroxyhexahydrofuro[3,2-b]furan-3-yl nitrate (291 mg, 1.53 mmol), NEt3 (770 mg, 7.62 mmol) and DMAP (62 mg, 0.51 mmol). The mixture was stirred at rt for 4 hrs. Water (30 mL) was added and the mixture was extracted with DCM (30 mL×3). The combined organic layers were washed with brine (20 mL×2), dried over $Na_2SO_4$. Then the resultant was filtered to collect the filtrate. The filtrate was concentrated. The crude product was purified by Flash Chromatography (PE/EA=1:1) to afford tert-butyl ((((3S,3aR,6R,6aS)-6-(nitrooxy)hexahydrofuro[3,2-b]furan-3-yl)oxy)carbonyl)glycinate (0.6 g mixture containing 50% (3R,3aS,6S,6aR)-6-hydroxyhexahydrofuro[3,2-b]furan-3-yl nitrate, 32% yield) as a colorless oil.

Step 3, ((((3S,3aR,6R,6aS)-6-(nitrooxy)hexahydrofuro[3,2-b]furan-3-yl)oxy)carbonyl)glycine was prepared as follows:

To a solution of tert-butyl ((((3S,3aR,6R,6aS)-6-(nitrooxy)hexahydrofuro[3,2-b]furan-3-yl)oxy)carbonyl)glycinate (0.6 g, 0.86 mmol) in DCM (10 mL) was added TFA (3 mL). The mixture was stirred at rt for 16 hrs, and then concentrated to afford ((((3S,3aR,6R,6aS)-6-(nitrooxy)hexahydrofuro[3,2-b]furan-3-yl)oxy)carbonyl)glycine (0.7 g, 99% yield) as a light-yellow oil. Mass spectrometry was conducted on the resultant compound, and the test results are as follows: Mass (m/z): 583.1 [2M−H]−.

Step 4, (3S,3aR,6R,6aS)-6-(nitrooxy)hexahydrofuro[3,2-b]furan-3-yl (2-chloro-2-oxoethyl)carbamate was prepared as follows:

To a solution of ((((3S,3aR,6R,6aS)-6-(nitrooxy)hexahydrofuro[3,2-b]furan-3-yl)oxy)carbonyl)glycine (0.7 g, 0.86 mmol) in DCM (10 mL) were added $(COCl)_2$ (164 mg, 1.29 mmol) and DMF (50 mg). The mixture was stirred at rt for 1 hr. Concentrated to afford (3S,3aR,6R,6aS)-6-(nitrooxy)hexahydrofuro[3,2-b]furan-3-yl (2-chloro-2-oxoethyl)carbamate (1.0 g, 99% yield) as a white solid. Used in the next step directly.

Step 5, (3S,3aR,6R,6aS)-6-(nitrooxy)hexahydrofuro[3,2-b]furan-3-yl (2-((2-((S)-1-(3-ethoxy-4-methoxyphenyl)-2-(methylsulfonyl)ethyl)-1,3-dioxoisoindolin-4-yl)amino)-2-oxoethyl)carbamate was prepared as follows:

To a solution of (3S,3aR,6R,6aS)-6-(nitrooxy)hexahydrofuro[3,2-b]furan-3-yl (2-chloro-2-oxoethyl)carbamate (1.0 g, 0.86 mmol) in DCM (20 mL) were added (S)-4-amino-2-(1-(3-ethoxy-4-methoxyphenyl)-2-(methylsulfonyl)ethyl)isoindoline-1,3-dione (200 mg, 0.478 mmol) and triethylamine (1.32 g, 13.1 mmol). The solution was stirred at rt for 2 h. Water (30 mL) was added and the mixture was extracted with DCM (20 mL×3). The combined organic layers were washed with brine (20 mL×3), dried over $Na_2SO_4$. Then the resultant was filtered to collect the filtrate. The filtrate was concentrated. The crude product was purified by prep-HPLC (ACN—$H_2O$, 0.1% FA) to afford (3S,3aR,6R,6aS)-6-(nitrooxy)hexahydrofuro[3,2-b]furan-3-yl (2-((2-((S)-1-(3-ethoxy-4-methoxyphenyl)-2-(methylsulfonyl)ethyl)-1,3-dioxoisoindolin-4-yl)amino)-2-oxoethyl)carbamate (Example 5) (8.5 mg, 1.4% yield) as a white solid. Mass spectrometry was conducted on the resultant compound, and the test results are as follows: Mass (m/z): 693.2 [M+H]+.

Example 6—the Compounds Inhibit the Activity of PDE

The inhibition of PDE4 (e.g., PDE4A, PDE4C) activity by the compounds (e.g., compound-1, compound-2, compound-3, compound-4, compound-5, and compound-6) are monitored using the PDE fluorescence polarization assay kits from BPS Bioscience (San Diego, USA) following the provided procedure. This assay is based on the selective binding of the fluorescent dye FAM-labelled AMP generated by the PDEs from the FAM-cAMP to its binding beads.

Briefly, compounds (2.5 ul of different concentrations diluted in the assay buffer) were mixed with 12.5 uL of the FAM-cAMP substrate (200 nM in the assay buffer) in a 384-well plate, 10 ul of the human recombinant PDE4A (BPS, Catalog #60340) or PDE4C (BPS, Catalog #60384) was added. The plate was incubated for 1 hr at room temperature. 50 ul of the binding agent for FAM-AMP was added. The mixture was incubated at room temperature for 20 min. The amount of binding agent bound FAM-AMP was measured by the fluorescence polarization method on the Envision spectrometer. The potency (IC50 value, Table1) of exemplified compounds was calculated from the dose-response curve using the 4-parameter non-linear regression fitting routine. The results show that compound-1, compound-2, compound-3, compound-4, and compound-5 are capable of effectively inhibiting PDE4.

TABLE 1

| PDE4A and PDE4C Inhibition Potency (IC50, nM) | | |
|---|---|---|
| Compound | IC50 for inhibiting PDE4A | IC50 for inhibiting PDE4C |
| compound-1 | 178 | 2230 |
| compound-2 | 308 | 2262 |
| compound-3 | 215 | 1025 |
| compound-4 | 710 | 109 |
| compound-5 | 38 | 826 |
| compound-6 | 214 | 734 |

Example 7—the Compounds Inhibit the Production of TNF-α and IFN-γQ

The inhibition of tumor necrosis factor alpha (TNF-α) and interferon gamma (IFN-γ) production by the compounds provided in the present disclosure in peripheral blood mononuclear cells or blood are monitored by following the protocols of Claveau et al (JPET, 310, 752-760, 2004). The compounds can inhibit expression of TNF-α and IFN-γ.

Example 8—the Compound Inhibits Acute Lung Injury in Mice

Mice (C57B16 on chow diet) are orally dosed with compound using 1% methyl cellulose as vehicle at 10 ml/kg dosing volume. After 30 min, LPS (30 ug/kg) is instilled nasally to induce inflammation and acute airway injury. TNFa level in plasma, and cell infiltration in BALF are monitored after 24 h LPS challenge. The compounds can mitigate acute long injury in mice.

Example 9—Production of Compound-6 after Oral Dosing of Compound-1 in Mice

Figure 10:
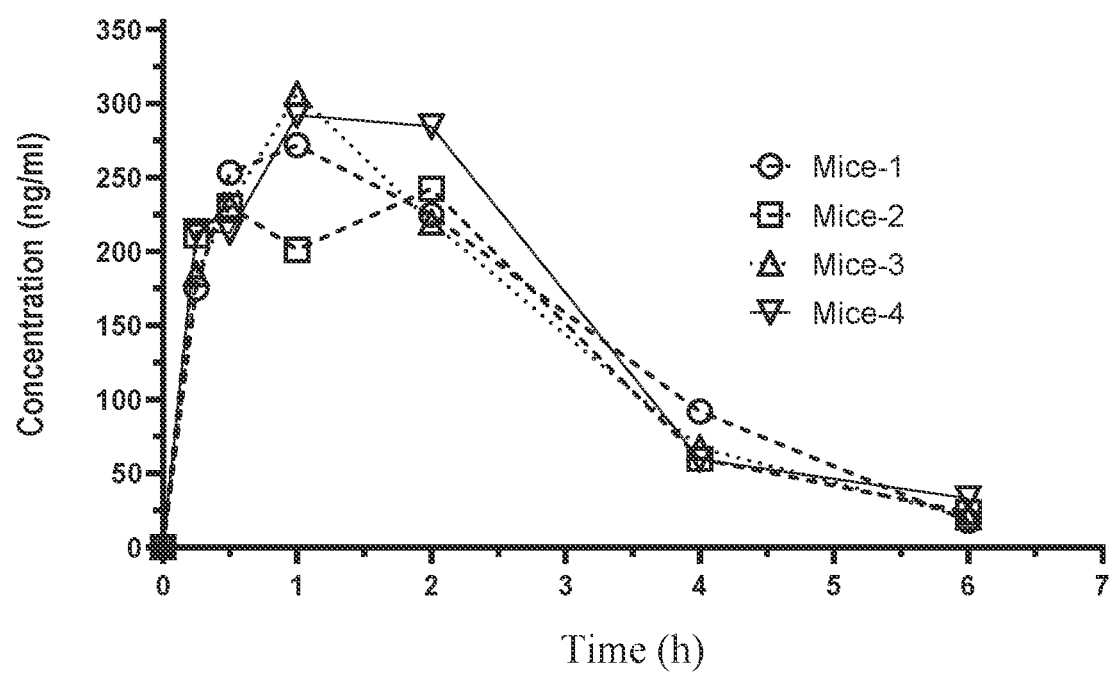
FIG. 10 is an analytical diagram that shows the blood level of compound-6 produced after dosing the compound-1 in mice according to some embodiments of the present disclosure.

FIG. 10 shows the blood level of compound-6 produced after dosing the compound-1 in mice. The exemplified compound-1 (formulated at 0.5 mg/mL in 0.5% carboxymethyl cellulose (CMC)/0.25% Tween-80 in water as a suspension) was dosed orally to 4 mice at 5 mg/kg. Compound-1 was bioactivated rapidly in the mice after oral dosing, forming a PDE4 inhibitory metabolite compound-6 consistently in every mice. Approximately 200 ng/mL of compound-6 was detected in the blood at 15 min. Compound-6 blood level peaked at approximately 250 ng/mL between 1 to 2 hrs, and mostly cleared to around 25 ng/mL at 6 hr. As seen from FIG. 10, the variation trend of the level of compound-6 in the blood is relatively stable. This kinetic profile of compound-6 blood level provides the opportunities to treat diseases that are responsive to compound-6 treatment, beyond dosing compound-6 directly, such as reducing the expected high Cmax-caused side effects from directly dosing compound-6.

Example 10—Production of Nitric Oxide from Bioactivation of Compound-1, Compound-2, and Compound-4

Compound-1 and compound-2 were formulated at 5 mg/ml, and compound-4 at 1 mg/ml in 1% CMC/0.5% Tween-80 in water as the vehicle. The total nitrates and total nitrite levels in plasma were quantified using the nitric oxide assay kit (ab65327, AbCam) following the provided protocols. The data were the mean (±SEM, 3 mice/group).

Figure 11:
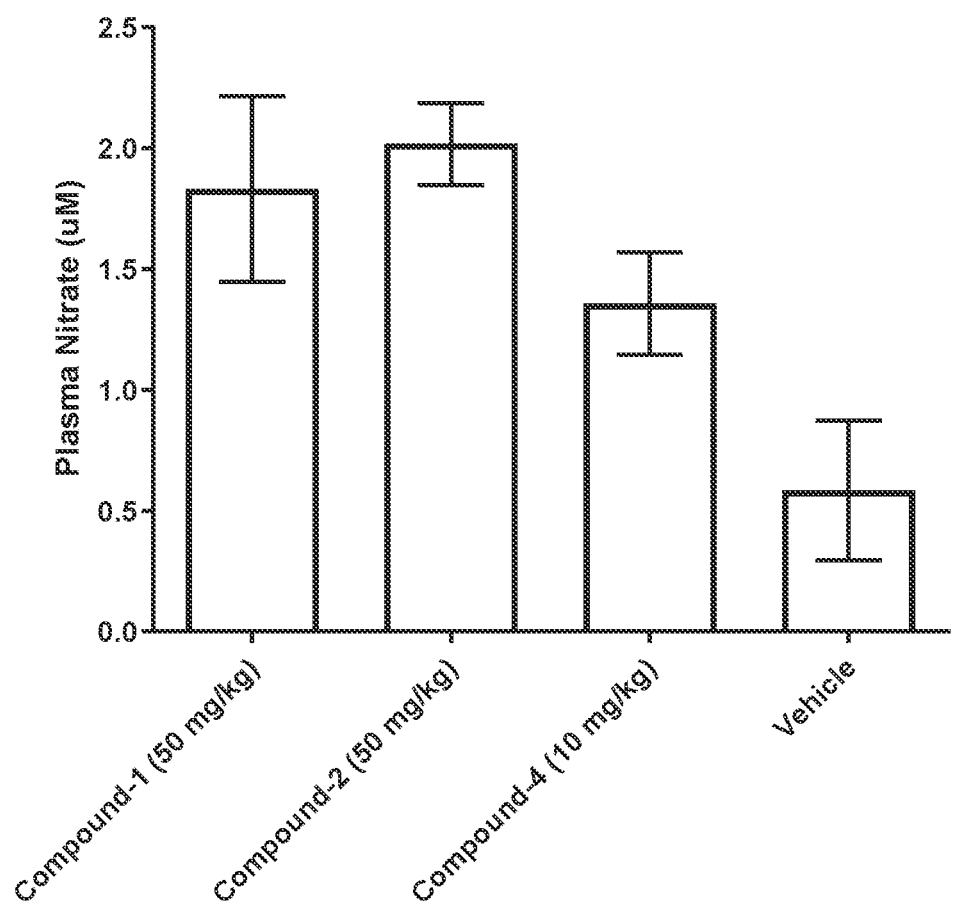
FIG. 11 is an analytical diagram that shows the nitrate levels in plasma at 1 h after dosing the compounds in mice according to some embodiments of the present disclosure.

FIG. 11 shows the nitrate levels in plasma at 1 h after dosing the compounds in mice. Significantly higher plasma nitrates were detected for each compound over the vehicle-treated mice. The data are indicative of the rapid bioactivation for each compound after oral dosing.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A compound represented by formula (I):

wherein the compound is configured to release nitric oxide (NO) and inhibit activity of a phosphodiesterase (PDE) when administered to a subject, wherein $L_1$ includes a functional group that is part or all of a NO releasing agent;

$L_2$ includes a functional group that is part or all of a PDE inhibitor, wherein $L_2$ is

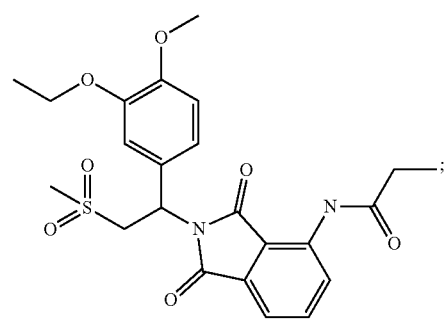 [SMILES: CCOc1cc(C(CS(C)(=O)=O)N2C(=O)c3cccc(NC(=O)CC)c3C2=O)ccc1OC]

and

—X— is a covalent bond, a non-covalent bond or a biradical that connects $L_1$ and $L_2$.

2. The compound of claim 1, wherein $L_1$ is —C(CH$_3$)$_2$—CH$_2$—ONO$_2$.

3. The compound of claim 1, wherein $L_1$ is —C(CH$_3$)—(CH$_2$—ONO$_2$)$_2$.

4. A compound represented by formula (II):

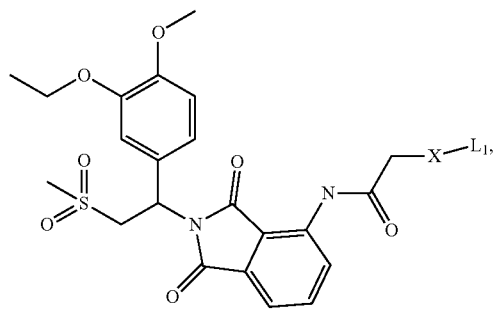

wherein —X— is a covalent bond, a non-covalent bond, or a biradical; and $L_1$ includes a functional group that is part or all of a nitric oxide (NO) releasing agent.

5. The compound of claim 4, wherein X includes O, C, N, S, or P.

6. The compound of claim 4, wherein —X— includes an ester bond, an amide bond, a sulfonamide bond, a sulfate bond, a phosphoramide bond, a phosphate bond, ketonic bond, or an arylene group.

7. The compound of claim 4, wherein $L_1$ includes one or more —$ONO_2$ groups.

8. The compound of claim 7, wherein $L_1$ is —$C(CH_3)_2$—$CH_2$—$ONO_2$.

9. The compound of claim 8, wherein the compound is

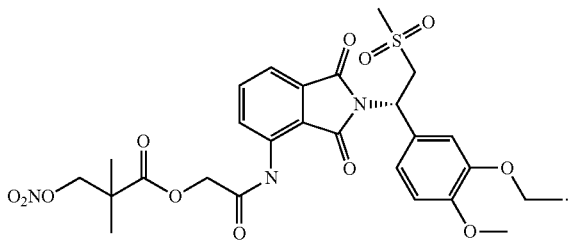

10. The compound of claim 8, wherein the compound is

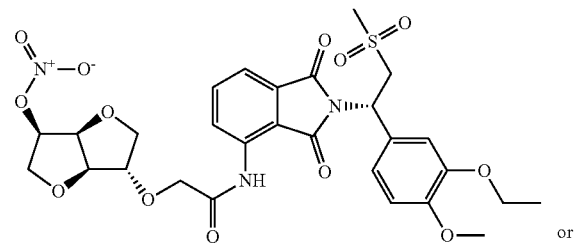

11. The compound of claim 7, wherein $L_1$ is —$C(CH_3)$—$(CH_2$—$ONO_2)_2$.

12. The compound of claim 11, wherein the compound is

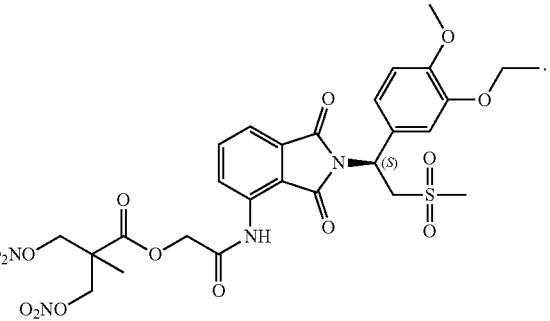

13. The compound of claim 7, wherein the compound is

14. The compound of claim 4, wherein the NO releasing agent is nitroglycerin (GTN), isosorbide dinitrate (ISDN), or pentaerythritol tetranitrate (PETN).

15. The compound of claim 4, wherein the compound is configured to release NO and inhibit activity of a phosphodiesterase (PDE) when administered to a subject.

16. The compound of claim 15, wherein the PDE includes PDE4.

17. A composition comprising the compound of claim 1 and a pharmaceutically acceptable carrier.

* * * * *